US012133956B2

(12) United States Patent
Kemps et al.

(10) Patent No.: US 12,133,956 B2
(45) Date of Patent: Nov. 5, 2024

(54) FLUID FLOWBACK PREVENTION IN A WYE-PIECE CONNECTOR

(71) Applicant: Fisher & Paykel Healthcare Limited, Auckland (NZ)

(72) Inventors: David Robert Kemps, Auckland (NZ); Sally Margaret Hensman, Auckland (NZ); Kevin Blake Powell, Auckland (NZ); Katie Fyfe, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 411 days.

(21) Appl. No.: 16/892,153

(22) Filed: Jun. 3, 2020

(65) Prior Publication Data
US 2020/0289780 A1    Sep. 17, 2020

Related U.S. Application Data

(63) Continuation of application No. 15/511,093, filed as application No. PCT/NZ2015/050151 on Sep. 17, 2015, now abandoned.
(Continued)

(51) Int. Cl.
*A61M 16/08* (2006.01)
*A61M 15/00* (2006.01)
(Continued)

(52) U.S. Cl.
CPC ...... *A61M 16/0833* (2014.02); *A61M 15/009* (2013.01); *A61M 16/0069* (2014.02);
(Continued)

(58) Field of Classification Search
CPC .............. A61M 16/08; A61M 16/0833; A61M 16/0875; A61M 16/0808; A61M 16/0816;
(Continued)

(56) References Cited

U.S. PATENT DOCUMENTS 3,612,048 A * 10/1971 Takaoka .............. A61M 16/104
128/205.12
3,814,103 A    6/1974 Fettel
(Continued)

FOREIGN PATENT DOCUMENTS

AU    2009245802 B2    11/2013
AU    2015264908 A1    12/2015
(Continued)

OTHER PUBLICATIONS

International Search Report and Written Opinion for PCT/NZ2015/050151 dated Feb. 10, 2016 in 22 pages.

*Primary Examiner* — Samchuan C Yao
*Assistant Examiner* — Nathan M Le
(74) *Attorney, Agent, or Firm* — Knobbe, Martens, Olson & Bear, LLP

(57) ABSTRACT

Connectors for respiratory assistance systems are disclosed that are configured to at least decrease the proportion of condensate that drains into an inspiratory conduit. The connectors include a setup that causes the portion of a wye-piece connected to an expiratory conduit to be positioned below the portion of the wye-piece connected to the inspiratory conduit. The connector can alternatively, or additionally, include a wye-piece that includes a ball attached to the wye-piece adjacent the inspiratory conduit port such that when the ball is connected to a medical stand, the expiratory conduit port is positioned below the inspiratory conduit port. The connector can alternatively or additionally include a circuit hanger that includes a cradles for both conduits and a ball attached to the circuit hanger adjacent the inspiratory conduit cradle such that when the ball is connected to a medical stand, the expiratory conduit cradle is positioned below the inspiratory conduit cradle. The connector can alternatively or additionally include a coaxial wye-piece that includes an inspiratory branch, an (Continued)

expiratory branch, and a patient end. The tip of the inspiratory branch that is internal to the coaxial wye-piece may have a lip and a narrowed diameter, features which obstruct or reduce condensate from entering the inspiratory branch and the inspiratory conduit regardless of the coaxial wye-piece orientation or position.

25 Claims, 11 Drawing Sheets

Related U.S. Application Data

(60) Provisional application No. 62/051,860, filed on Sep. 17, 2014.

(51) Int. Cl.
*A61M 16/00* (2006.01)
*A61M 16/10* (2006.01)
*A61M 16/16* (2006.01)

(52) U.S. Cl.
CPC ........ *A61M 16/08* (2013.01); *A61M 16/0808* (2013.01); *A61M 16/0841* (2014.02); *A61M 16/0875* (2013.01); *A61M 16/109* (2014.02); *A61M 16/1095* (2014.02); *A61M 16/16* (2013.01); *A61M 2205/3368* (2013.01); *A61M 2205/3653* (2013.01); *A61M 2209/082* (2013.01); *A61M 2209/084* (2013.01)

(58) Field of Classification Search
CPC .............. A61M 39/10; A61M 16/0069; A61M 16/0841; A61M 16/10875; A61M 16/109; A61M 16/1095; A61M 16/16; A61M 15/009
See application file for complete search history.

(56) References Cited

U.S. PATENT DOCUMENTS

| | | | |
|---|---|---|---|
| 3,903,884 | A | 9/1975 | Huston et al. |
| 4,020,834 | A | 5/1977 | Bird |
| 4,248,217 | A | 2/1981 | Brisson |
| 4,333,451 | A | 6/1982 | Paluch |
| 4,557,261 | A | 12/1985 | Rugheimer |
| 4,558,708 | A | 12/1985 | Labuda et al. |
| 4,580,556 | A | 4/1986 | Kondur |
| 4,668,218 | A | 5/1987 | Virtanen |
| 4,723,543 | A | 2/1988 | Beran |
| 4,773,448 | A | 9/1988 | Francis |
| 4,787,655 | A | 11/1988 | Gross et al. |
| 4,817,822 | A | 4/1989 | Rand et al. |
| 4,819,629 | A | 4/1989 | Jonson |
| 4,827,921 | A | 5/1989 | Rugheimer |
| 5,036,840 | A | 8/1991 | Wallace |
| 5,062,420 | A | 11/1991 | Levine |
| 5,099,833 | A | 3/1992 | Michaels |
| 5,178,138 | A | 1/1993 | Walstrom et al. |
| 5,195,980 | A | 3/1993 | Catlin |
| 5,228,436 | A | 3/1993 | Parkin |
| 5,297,543 | A | 3/1994 | Larson et al. |
| D362,503 | S | 9/1995 | Cook et al. |
| 5,460,172 | A | 10/1995 | Eckerbom et al. |
| 5,474,058 | A | 12/1995 | Lix |
| 5,546,930 | A | 8/1996 | Wikefeldt |
| 5,720,282 | A | 2/1998 | Wright |
| 5,735,271 | A | 4/1998 | Lorenzen et al. |
| 5,776,117 | A | 7/1998 | Haselhorst et al. |
| 5,988,164 | A | 11/1999 | Paluch |
| 6,102,038 | A | 8/2000 | DeVries |
| 6,209,539 | B1 | 4/2001 | Loescher et al. |
| D492,030 | S | 6/2004 | Rani |
| D492,773 | S | 7/2004 | Elllingboe et al. |
| D519,632 | S | 4/2006 | Bayron et al. |
| 7,152,597 | B2 | 12/2006 | Bathe |
| 7,162,921 | B2 | 1/2007 | Gerder et al. |
| D547,447 | S | 7/2007 | Bruce et al. |
| 7,634,998 | B1 | 12/2009 | Fenley |
| 7,841,341 | B2 | 11/2010 | Dhuper et al. |
| 7,926,484 | B2 | 4/2011 | Dhuper et al. |
| D649,240 | S | 11/2011 | Lewis et al. |
| 8,151,794 | B2 | 4/2012 | Meyer et al. |
| D672,459 | S | 12/2012 | Miller |
| D685,906 | S | 7/2013 | Dale et al. |
| D689,187 | S | 9/2013 | Kruger |
| D691,717 | S | 10/2013 | McLean et al. |
| 8,720,435 | B2 | 5/2014 | Gallem et al. |
| 8,746,241 | B2 | 6/2014 | Cavendish |
| D709,612 | S | 7/2014 | Lewis |
| D723,681 | S | 3/2015 | Ingram et al. |
| D747,473 | S | 1/2016 | Martin et al. |
| 9,539,401 | B2 | 1/2017 | Tatkov |
| 10,143,818 | B2 | 12/2018 | Martin et al. |
| 10,369,313 | B2 | 8/2019 | White et al. |
| 10,532,173 | B2 | 1/2020 | Tatkov |
| 11,351,325 | B2 | 6/2022 | Martin et al. |
| 11,439,786 | B2 | 9/2022 | Tatkov |
| 2003/0116167 | A1 | 6/2003 | Hooser |
| 2004/0016302 | A1 | 1/2004 | Misholi et al. |
| 2004/0089296 | A1 | 5/2004 | Bowden |
| 2004/0168690 | A1 | 9/2004 | Payne |
| 2005/0188990 | A1 | 9/2005 | Fukunaga et al. |
| 2005/0229928 | A1 | 10/2005 | Irvi et al. |
| 2006/0173420 | A1 | 8/2006 | Fangrow, Jr. |
| 2006/0283447 | A1 | 12/2006 | Dhuper et al. |
| 2007/0083677 | A1* | 4/2007 | Cecka .............. A61M 16/0841 710/1 |
| 2007/0101994 | A1 | 5/2007 | Waters |
| 2007/0193581 | A1 | 8/2007 | Laurila et al. |
| 2008/0077063 | A1 | 3/2008 | Meyer et al. |
| 2008/0264412 | A1* | 10/2008 | Meyer ............... A61M 16/0841 128/200.22 |
| 2008/0264418 | A1 | 10/2008 | Schermeier et al. |
| 2009/0105692 | A1 | 4/2009 | Lopez et al. |
| 2009/0124983 | A1 | 5/2009 | Ferrari |
| 2009/0301476 | A1 | 12/2009 | Korneff et al. |
| 2010/0071688 | A1 | 3/2010 | Dwyer |
| 2010/0071695 | A1 | 3/2010 | Thiessen |
| 2010/0139653 | A1 | 6/2010 | Schloss |
| 2010/0163051 | A1* | 7/2010 | Brewer ............. A61M 16/0833 128/207.14 |
| 2010/0242622 | A1 | 9/2010 | Weckstrom |
| 2011/0088696 | A1 | 4/2011 | Ratner |
| 2011/0146670 | A1 | 6/2011 | Gallem et al. |
| 2011/0284007 | A1 | 11/2011 | Pierre |
| 2012/0180791 | A1 | 7/2012 | Ciccone et al. |
| 2012/0255545 | A1 | 10/2012 | Meyer et al. |
| 2013/0081616 | A1* | 4/2013 | Tatkov ............. A61M 16/0841 128/201.13 |
| 2013/0146053 | A1 | 6/2013 | Mazela et al. |
| 2013/0269686 | A1 | 10/2013 | Pezzano et al. |
| 2014/0166011 | A1* | 6/2014 | Pierro ............... A61M 16/0825 128/204.14 |
| 2014/0276178 | A1 | 9/2014 | Simon |
| 2015/0021909 | A1 | 1/2015 | Gulliver et al. |
| 2015/0314093 | A1 | 11/2015 | Chiu |
| 2016/0038700 | A1 | 2/2016 | White et al. |
| 2017/0007797 | A1 | 1/2017 | Islava |
| 2017/0100558 | A1 | 4/2017 | Dhuper et al. |
| 2017/0246417 | A1 | 8/2017 | Kemps et al. |
| 2018/0272084 | A1 | 9/2018 | Reiner |
| 2019/0111229 | A1 | 4/2019 | Martin et al. |
| 2021/0138176 | A1 | 5/2021 | Meech |
| 2022/0339388 | A1 | 10/2022 | Martin et al. |
| 2022/0409842 | A1 | 12/2022 | Tatkov |

FOREIGN PATENT DOCUMENTS

| | | |
|---|---|---|
| CN | 201912587 U | 8/2011 |
| DE | 3703441 A1 | 8/1988 |
| DE | 102007009449 B3 | 1/2008 |

(56) References Cited

FOREIGN PATENT DOCUMENTS

| | | |
|---|---|---|
| DE | 202011107902 U1 | 1/2012 |
| EP | 0604399 A1 | 6/1994 |
| EP | 1820528 | 8/2007 |
| EP | 2044921 B1 | 7/2011 |
| FR | 2725627 | 10/1994 |
| GB | 750672 A | 6/1956 |
| GB | 1290484 A | 9/1972 |
| GB | 1317315 A | 5/1973 |
| GB | 2412877 | 10/2005 |
| JP | 2004-033550 A | 2/2004 |
| WO | WO 1999/059517 | 11/1999 |
| WO | WO 2003/041780 | 5/2003 |
| WO | WO 2005/048982 | 6/2005 |
| WO | WO 2012/030232 A1 | 3/2012 |
| WO | WO 2013/147623 | 10/2013 |
| WO | WO 2013/162386 | 10/2013 |
| WO | WO 2014/116122 | 7/2014 |
| WO | WO 2015/174859 | 11/2015 |
| WO | WO 2017/037660 A1 | 3/2017 |

\* cited by examiner

FLUID FLOWBACK PREVENTION IN A WYE-PIECE CONNECTOR

INCORPORATION BY REFERENCE TO ANY PRIORITY APPLICATIONS

This application is a continuation of U.S. patent application Ser. No. 15/511,093, filed Mar. 14, 2017, which is a U.S. National Phase of International Patent Application No. PCT/NZ2015/050151, filed Sep. 17, 2015, which claims the priority benefit of U.S. Provisional Application No. 62/051,860, filed Sep. 17, 2014, the entirety of which is hereby incorporated by reference herein. Any and all applications for which a foreign or domestic priority claim is identified in the Application Data Sheet as filed with the present application are hereby incorporated by reference under 37 CFR 1.57.

BACKGROUND

Technical Field

The present disclosure generally relates to respiratory assistance systems. More particularly, the present disclosure relates to conduit connectors for respiratory assistance systems.

Description of the Related Art

A respiratory assistance system may be used to provide respiratory gases to a patient from a gases source via an inspiratory conduit in fluid communication between the gases source and a patient interface. Examples of a patient interface may include an oral mask, a nasal mask, a nasal cannula, a tracheal mask, or an endotracheal tube. In a respiratory assistance system where the gases source is a ventilator, gases exhaled by the patient into the patient interface may be returned via an expiratory conduit in fluid communication between the patient interface and the ventilator. The inspiratory conduit and the expiratory conduit may be connected to the patient interface via a wye-piece.

A respiratory assistance system may include a humidification device to condition respiratory gases provided to the patient. The humidification device may include a humidification chamber containing liquid and a heater adjacent the humidification chamber to heat the liquid to produce vapor. The humidification device may be positioned in the fluid communication path between the gases source and the patient interface to heat and/or humidify respiratory gases prior to delivery via the inspiratory conduit to the patient interface. Respiratory gases delivered to a patient at 100% relative humidity and 37° C. mimic the properties resulting from the transformation of air that occurs as it passes through the patient's nose to the lungs. This promotes efficient gas exchange and ventilation in the lungs, aids defense mechanisms in the airway, and increases patient comfort during treatment.

An inspiratory conduit for use in a respiratory assistance system with a humidification device may include a heating component, such as a heater wire, to keep heated and humidified respiratory gases delivered via the inspiratory conduit to the patient interface warm and to reduce formation of condensate in the inspiratory conduit. However, a heated inspiratory conduit may be connected to an unheated wye-piece and/or an unheated patient interface. The passage of heated and humidified respiratory gases through an unheated wye-piece and/or an unheated patient interface can increase formation of condensate in the respiratory assistance system. Vapor present in gases exhaled by a patient can also increase formation of condensate in a respiratory assistance system.

SUMMARY

Condensate that forms in a respiratory assistance system may drain in one or more of three directions: toward the patient, into the inspiratory conduit toward the humidification device, and/or into the expiratory conduit toward the ventilator. Condensate that drains toward the patient may reduce effectiveness of respiratory treatment and/or decrease patient comfort. Thus, caregivers often may arrange the inspiratory conduit, the expiratory conduit, and/or the patient interface to reduce the amount of condensate that drains toward the patient. Condensate that drains toward the humidification device may cause at least partial occlusion of the inspiratory conduit which could reduce effective of respiratory treatment. Condensate that drains toward the ventilator may damage the ventilator.

In a respiratory assistance system where the expiratory conduit includes features adapted to reduce condensate in gases delivered via the expiratory conduit to a gases source, it may be useful to decrease the proportion of condensate that drains toward the patient and/or into the inspiratory conduit by increasing the proportion of condensate that drains into the expiratory conduit. Embodiments are disclosed of connectors configured to at least decrease the proportion of condensate that drains into the inspiratory conduit by causing the portion of the wye-piece connected to the expiratory conduit to be positioned below the portion of the wye-piece connected to the inspiratory conduit. This arrangement allows condensate that reaches the wye-piece to naturally drain through gravitational force into the expiratory.

According to an embodiment, a connector comprises a wye-piece, the wye-piece comprising a port for an inspiratory conduit, a port for an expiratory conduit, a port for a patient interface, a body formed by a fluid passageway between the port for the inspiratory conduit and the port for the patient interface and a fluid passageway between the port for the expiratory conduit and the port for the patient interface, and a ball for connecting the wye-piece to a medical stand, wherein the ball is attached to the body adjacent the port for the inspiratory conduit such that when the ball is connected to a medical stand, the port for the expiratory conduit is positioned below the port for the inspiratory conduit.

The ball may be attached directly to the body of the wye-piece, or it may be attached to a stem that is attached to the body of the wye-piece. The ball, or ball and stem, may be integrally formed with the body, detachable from the body, or formed separately from and securely adhered to the body.

According to an another example embodiment, a connector comprises a circuit hanger, the circuit hanger comprising a body, the body comprising a cradle for an inspiratory conduit, a cradle for an expiratory conduit, and a ball for connecting the circuit hanger to a medical stand, wherein the ball is attached to the body adjacent the cradle for the inspiratory conduit such that when the ball is connected to a medical stand, the cradle for the expiratory conduit is positioned below the cradle for the inspiratory conduit.

The ball may be attached directly to the body of the circuit hanger, or it may be attached to a stem that is attached to the body of the circuit hanger. The ball, or ball and stem, may be integrally formed with the body, detachable from the body, or formed separately from and securely adhered to the body.

The medical stand may be configured to securely hold the ball of the connector so that the connector may be held in a specific orientation or position. The medical stand may have a mechanism that allows the orientation or position of the connector to be changed by a user. The medical stand may have a ball-holding portion that is configured to attach to, hold, or secure the ball of a connector that comprises a circuit hanger. The ball-holding portion may be able to be tightened or loosened so that a user may change the orientation or position of the connector, such as by first loosening the ball-holding portion, changing the orientation or position of the connector to the desired orientation or position, and then tightening the ball-holding portion to secure the connector in the desired orientation or position.

According to an another example embodiment, a connector comprises a coaxial wye-piece, the coaxial wye-piece comprising a body, the body comprising an inspiratory branch with an inspiratory conduit port, an expiratory branch with an expiratory conduit port, a patient end with a patient interface port, a fluid passageway between the inspiratory conduit port and the patient interface port, and a fluid passage between the expiratory conduit port and the patient interface port. The inspiratory branch may comprise a tip that extends into the fluid passageway between the expiratory conduit port and the patient interface port of the body. The tip of the inspiratory branch may comprise a lip, the lip configured to obstruct or impede a condensate from draining toward the inspiratory branch. An MDI or pressure port may also be located on the inspiratory branch at a location far enough away from the inspiratory conduit port so that the inspiratory conduit port may be connected to an inspiratory conduit. The patient end may have a solid wall between an inner surface and an outer surface, as well as a dual taper design that allows the patient end to act as a male or female connector.

According to an another example embodiment, a connector comprises a coaxial wye-piece, the coaxial wye-piece comprising a body, the body comprising an inspiratory branch with an inspiratory conduit port, an expiratory branch with an expiratory conduit port, a patient end with a patient interface port, a fluid passageway between the inspiratory conduit port and the patient interface port, and a fluid passage between the expiratory conduit port and the patient interface port. The inspiratory branch may comprise a tip that extends into the fluid passageway between the expiratory conduit port and the patient interface port of the body. The tip of the inspiratory branch may comprise a lip, the lip configured to obstruct or impede a condensate from draining toward the inspiratory branch. An MDI or pressure port may also be located on the inspiratory branch at a location far enough away from the inspiratory conduit port so that the inspiratory conduit port may be connected to an inspiratory conduit. The patient end may have a gap in a wall between an inner surface and an outer surface, as well as a dual taper design that allows the patient end to act as a male or female connector. The gap may preserve the dual taper design while allowing less material to be used.

According to an another example embodiment, a connector comprises a coaxial wye-piece, the coaxial wye-piece comprising a body, the body comprising an inspiratory branch with an inspiratory conduit port, an expiratory branch with an expiratory conduit port, a patient end with a patient interface port, a fluid passageway between the inspiratory conduit port and the patient interface port, and a fluid passage between the expiratory conduit port and the patient interface port. The body may further comprise an inner coaxial inspiratory tube that extends from the inspiratory branch into the fluid passageway between the expiratory conduit port and the patient interface port. The inner coaxial inspiratory tube may be directed towards the patient end and may extend all up to the patient interface port of the patient end. The inner coaxial inspiratory tube may obstruct or impede a condensate from draining toward the inspiratory branch, and it may also direct the flow of inspiratory gas towards the patient end. The inspiratory branch may comprise a tip that extends into the fluid passageway between the expiratory conduit port and the patient interface port of the body. The tip of the inspiratory branch may comprise a lip, the lip configured to obstruct or impede a condensate from draining toward the inspiratory branch. An MDI or pressure port may also be located on the inspiratory branch at a location far enough away from the inspiratory conduit port so that the inspiratory conduit port may be connected to an inspiratory conduit.

BRIEF DESCRIPTION OF THE DRAWINGS

These and other aspects of the present disclosure will be described with reference to the following drawings, which should be considered illustrative but not limiting.

DETAILED DESCRIPTION

Terms

Figure 1:
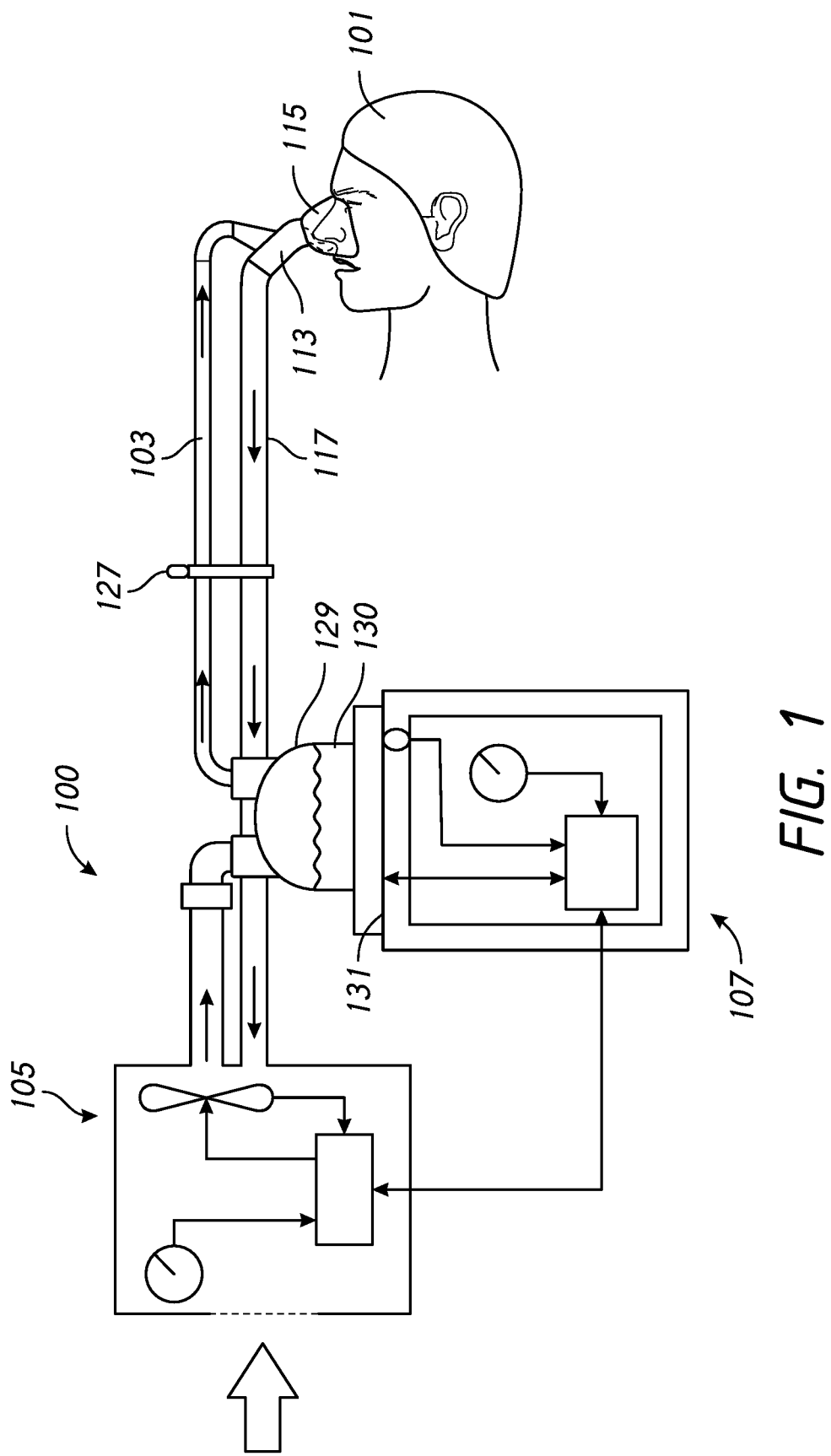
FIG. 1 is a diagram of an example respiratory assistance system that may be used to provide respiratory gases to a patient.

The term conduit refers to any tube, channel, or passageway that may be used in a respiratory assistance system. Conduits that may be used to carry respiratory gas in a respiratory assistance system include smooth-bore conduits, which may have inner wall surfaces that are smooth. The width of the conduit wall of a smooth-bore conduit may be constant. An example of a smooth-bore conduit is disclosed in International Application No. PCT/NZ2015/050028, which is herein incorporated by reference in its entirety. Conduits that may be used to carry respiratory gas in a respiratory assistance system may also include conduits with inner wall surfaces that are not smooth. Examples of such conduits include corrugated conduits. A corrugated conduit may have a series of parallel ridges or grooves. A corrugated conduit may also be known as a concertina or bellows conduit. Other types of conduits with inner wall surfaces that are not smooth may have helical or spiraling ridges or grooves. A conduit may be designed to possess a combination of features from different conduit types. For example, a conduit may have a smooth bore while retaining a series of parallel ridges or grooves on the exterior of the conduit. Such a conduit would have a smooth inner wall surface and a wall width that is non-constant while retaining some of the benefits of a corrugated conduit, which are described in further detail below.

There may be certain benefits associated with a corrugated conduit. For example, the sizing and/or spacing of parallel ridges or grooves in a corrugated conduit may allow for specially-designed medical connectors that fit the ridges and grooves in order to hold or grasp the corrugated conduit in place. A corrugated conduit may allow for increased flexibility and bending. The parallel ridges or grooves present in a corrugated conduit may trap or hinder mobile condensate, making a corrugated conduit well-suited for preventing condensate from freely moving in a respiratory assistance system.

There may be certain benefits associated with the use of smooth-bore conduits. The smooth inner wall surface of smooth-bore conduits may allow for the flow of gas with less resistance and reduced turbulence. The smooth inner wall surface of smooth-bore conduits may allow for higher velocity gas flow. This may make smooth-bore conduits well-suited for high flow respiratory therapy. A connector designed to reduce the mobility of condensate within a respiratory assistance system may greatly improve the usability of the system with a smooth-bore conduit.

The term branch refers to a projection of a connector in a respiratory assistance system. For example, a connector may have a Y-shape. One end of this connector may be referred to as the inspiratory branch because it is designed to connect to, and interface with, the inspiratory conduit. Another end of this connector may be referred to as the expiratory branch because it is designed to connect to, and interface with, the expiratory conduit. A branch may have a port or opening in it which may allow the branch to be fluidly connected to another object. For example, an inspiratory branch may have an inspiratory conduit port for connecting to the inspiratory conduit and an expiratory branch may have an expiratory conduit port for connecting to the expiratory conduit.

The term metered-dose inhaler (MDI) port refers to a port in a respiratory assistance system that is configured to connect to, or interface with, a metered-dose inhaler, which is a device designed to deliver a specific amount of medication to the lungs of a patient. A metered-dose inhaler may be configured to deliver medication in aerosol form through the MDI port into the inspiratory gas flow of a respiratory assistance system.

General Respiratory Assistance System (FIG. 1)

FIG. 1 is a diagram of an example respiratory assistance system 100 that may be used to provide respiratory gases to a patient 101. The respiratory assistance system 100 comprises a gases source 105 in fluid communication with a patient interface 115 via an inspiratory conduit 103 and an expiratory conduit 117. In some configurations, the gases source 105 comprises a ventilator. The inspiratory conduit 103 and the expiratory conduit 117 are connected to the patient interface 115 via a wye-piece 113.

In the configuration shown, the respiratory assistance system 100 also comprises a humidification device 107 to condition respiratory gases provided to the patient 101. The humidification device 107 is positioned in the fluid communication path between the gases source 105 and the patient interface 115 to heat and/or humidify respiratory gases prior to delivery via the inspiratory conduit 103 to the patient interface 115. The humidification device 107 comprises a humidification chamber 129 containing a liquid 130 and a heater 131 adjacent to the humidification chamber 129 to heat the liquid 130 to produce vapor that humidifies respiratory gases passing over the liquid 130. In some configurations, the gases source 105 and the humidification device 107 are located within a common housing and/or comprise components of a single apparatus. In some configurations, the gases source 105 is connected directly to the patient interface 115 via the inspiratory conduit 103 with no intervening humidification device.

In some configurations, the inspiratory conduit 103 includes a heating component, such as a heater wire, to keep heated and humidified respiratory gases delivered via the inspiratory conduit 103 to the patient interface 115 warm and to reduce formation of condensate in the inspiratory conduit 103. In some configurations, the wye-piece 113 and/or the patient interface 115 might not include a similar heating feature, so vapor present in heated and humidified respiratory gases delivered via the inspiratory conduit 103 to the wye-piece 113 may condense in the wye-piece 113 and/or the patient interface 115. In some configurations, vapor present in gases exhaled by the patient 101 may condense in the wye-piece 113 and/or the patient interface 115.

Condensate that forms in the respiratory assistance system 100, particularly but not exclusively in the wye-piece 113 and/or the patient interface 115, may drain in one or more of three directions: toward the patient 101, into the inspiratory conduit 103 toward the humidification device 107, and/or into the expiratory conduit 117 toward the gases source 105. It may be considered undesirable to allow condensate to drain toward the patient 101, because liquid introduced to the face or airway of the patient 101 may reduce effectiveness of respiratory treatment and/or decrease comfort. It may be considered undesirable to allow condensate to drain toward the humidification device 107, because condensate formed of vapor present in gases exhaled by the patient may cause at least partial occlusion of the inspiratory conduit 103 which could reduce effective of respiratory treatment. It may be considered undesirable to allow condensate to drain toward the gases source 105, because liquid may damage the gases source 105.

In some configurations, the expiratory conduit 117 may include features configured to reduce condensate in gases delivered through the expiratory conduit 117 to the gases source 105. See, for example, the embodiments and features disclosed in U.S. Patent Application Publication No. 2013/0098360. In some configurations, it may be appropriate to decrease the proportion of condensate that drains toward the patient 101 and into the inspiratory conduit 103 by increasing the proportion of condensate that drains into the expiratory conduit 117. Multiple embodiments of connectors are disclosed that at least decrease the proportion of condensate that drains into the inspiratory conduit 103 by causing the portion of the wye-piece 113 connected to the expiratory conduit 117 to be positioned below the portion of the wye-piece 113 connected to the inspiratory conduit 103. Other embodiments of connectors are disclosed that at least decrease the proportion of condensate that drains into the inspiratory conduit 103 regardless of the orientation or positioning of the inspiratory conduit 103 relative to the expiratory conduit 117.

Figure 2:
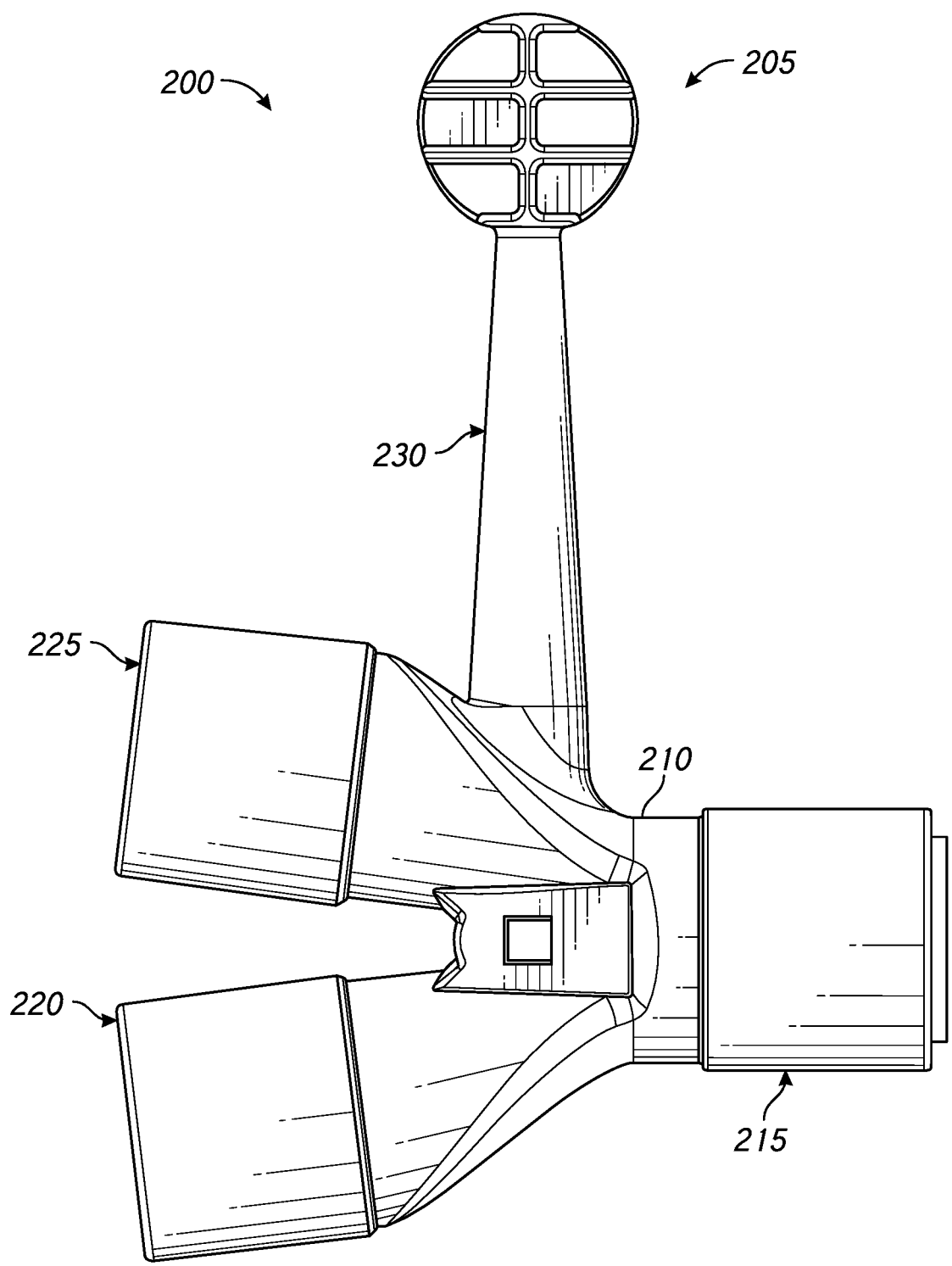
FIG. 2 is a diagram of a connector for a respiratory assistance system according to an example embodiment in which the connector comprises a wye-piece.

Wye-Piece Connector With Ball (FIG. 2)

FIG. 2 is a picture of a connector for the respiratory assistance system 100 according to a first example embodiment, where the connector comprises a wye-piece 200. The wye-piece 200 comprises a body 210, an inspiratory conduit port 225, an expiratory conduit port 220, and a patient interface port 215. The body 210 includes a fluid passageway between the inspiratory conduit port 225 and the patient interface port 215 and a fluid passageway between the expiratory conduit port 220 and the patient interface port 215. The wye-piece 200 comprises a ball 205 for connecting the wye-piece 200 to a medical stand. The ball 205 is attached to the body 210 adjacent the inspiratory conduit port 225 such that when the ball 205 is connected to a medical stand, the expiratory conduit port 220 is positioned below the inspiratory conduit port 225.

In the configuration shown, the ball 205 is attached to a stem 230 and the stem 230 is attached to the body 210. The ball 205 may be integrally formed with the stem 230. The ball 205 may be detachable from the stem 230. The ball 205 may be formed separately from and securely adhered to the stem 230. The stem 230 may be integrally formed with the body 210. The stem 230 may be detachable from the body 210. The stem 230 may be formed separately from and securely adhered to the body 210. Any combination of the above types of attachment between the ball 205 and the stem 230 and between the stem 230 and the body 210 may be used.

In some configurations, the ball 205 is attached directly to the body 210. The ball 205 may be integrally formed with the body 210. The ball 205 may be detachable from the body 210. The ball 205 may be formed separately and securely adhered to the body 210.

In use, the wye-piece 113 is replaced by the wye-piece 200, such that the inspiratory conduit 103 is connected to the inspiratory conduit port 225, the expiratory conduit 117 is connected to the expiratory conduit port 220, and the patient interface 115 is connected to the patient interface port 215. In use, the wye-piece 200 is connected, via the ball 205, to a medical stand, which positions the expiratory conduit port 220 below the inspiratory conduit port 225, which causes the expiratory conduit 117 to be positioned below the inspiratory conduit 103, at least causing a larger proportion of any condensate formed in the respiratory assistance system 100 that reaches the wye-piece 200 to drain into the expiratory conduit 117 than into the inspiratory conduit 103.

Figure 3A:
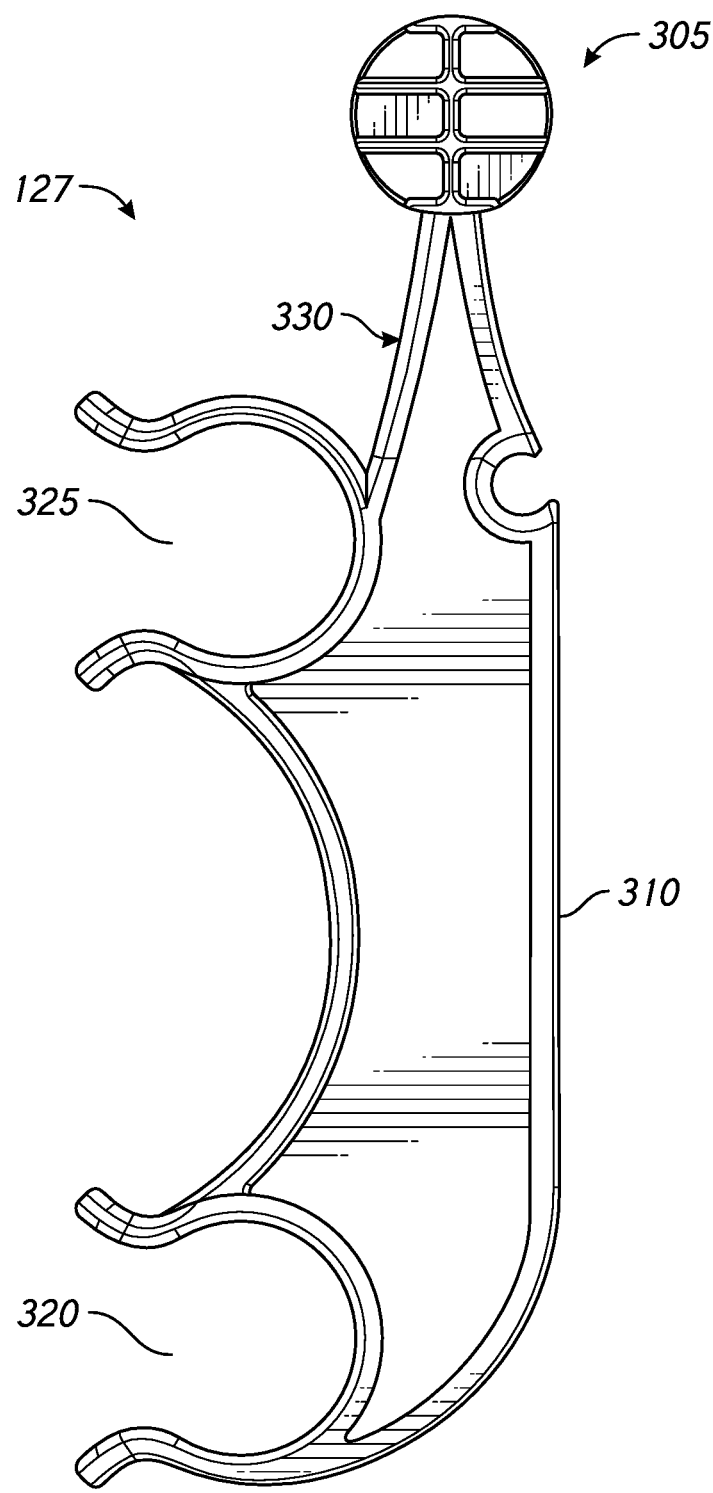
FIG. 3A is a diagram of a connector for a respiratory assistance system according to an example embodiment in which the connector comprises a circuit hanger.

Circuit Hanker Connector With Ball (FIG. 3A)

FIG. 3A is a picture of a connector for the respiratory assistance system 100 according to a second example embodiment, where the connector comprises a circuit hanger 127. The circuit hanger 127 includes a body 310, and the body 310 includes an inspiratory conduit cradle 325 and an expiratory conduit cradle 320. The circuit hanger 127 comprises a ball 305 for connecting the circuit hanger 127 to a medical stand. The ball 305 is attached to the body 310 adjacent the inspiratory conduit cradle 325 such that when the ball 305 is connected to a medical stand, the expiratory conduit cradle 320 is positioned below the inspiratory conduit cradle 325.

In the configuration shown, the ball 305 is attached to a stem 330 and the stem 330 is attached to the body 310. The ball 305 may be integrally formed with the stem 330. The ball 305 may be detachable from the stem 330. The ball 305 may be formed separately from and securely adhered to the stem 330. The stem 330 may be integrally formed with the body 310. The stem 330 may be detachable from the body 310. The stem 330 may be formed separately from and securely adhered to the body 310. Any combination of the above types of attachment between the ball 305 and the stem 330 and between the stem 330 and the body 310 may be used.

In some configurations, the ball 305 is attached directly to the body 310. The ball 305 may be integrally formed with the body 310. The ball 305 may be detachable from the body 310. The ball 305 may be formed separately from and securely adhered to the body 310.

Referring again to FIG. 1, the circuit hanger 127 is shown connected to the inspiratory conduit 103 and the expiratory conduit 117, such that the inspiratory conduit 103 passes through, or is held by, the inspiratory conduit cradle 325 and the expiratory conduit 117 passes through, or is held by, the expiratory conduit cradle 320. In use, the circuit hanger 127 is connected, via the ball 305, to a medical stand, which positions the expiratory conduit cradle 320 below the inspiratory conduit cradle 325, which causes the expiratory conduit 117 to be positioned below the inspiratory conduit 103, at least causing a larger proportion of any condensate formed in the respiratory assistance system 100 that reaches the wye-piece 113 to drain into the expiratory conduit 117 than into the inspiratory conduit 103.

In some configurations, the inspiratory conduit cradle 325 may include a shape suitable for holding the inspiratory conduit 103 that is different from the shape of the inspiratory conduit cradle 325 depicted in FIG. 3A. In some configurations, the expiratory conduit cradle 320 may include a shape suitable for holding the expiratory conduit 117 that is different from the shape of the expiratory conduit cradle 320 depicted in FIG. 3A. In a preferred configuration, the inspiratory conduit cradle 325 may include a different shape from the expiratory conduit cradle 320, which may help ensure that the connections are correct, i.e. the inspiratory conduit 103 is connected to the inspiratory conduit cradle 325 and the expiratory conduit 117 is connected to the expiratory conduit cradle 320. In some configurations, the inspiratory conduit cradle 325 and the expiratory conduit cradle 320 may include the same shape.

In some configurations, the inspiratory conduit cradle 325 may be adapted to connect to a circuit accessory that is adapted to attach to the inspiratory conduit 103. In some configurations, the expiratory conduit cradle 320 may be adapted to connect to a circuit accessory that is adapted to attach to the expiratory conduit 117. For example, but without limitation, either or both of the inspiratory conduit cradle 325 or the expiratory conduit cradle 320 may be adapted to connect to any one or more of the locking clips disclosed in U.S. Patent Application Publication No. 2014/0236041. In a preferred configuration, the inspiratory conduit cradle 325 is adapted to connect to a different type of circuit accessory from a type of circuit accessory to which the expiratory conduit cradle 320 is adapted to connect, which may help ensure that the inspiratory conduit 103 is connected to the inspiratory conduit cradle 325 and the expiratory conduit 117 is connected to the expiratory conduit cradle 320. In some configurations, the inspiratory conduit cradle 325 and the expiratory conduit cradle 320 are adapted to connect to the same type of circuit accessory.

In some configurations, the body 310 may be adapted to connect to a circuit accessory that is adapted to attach to both the inspiratory conduit 103 and to the expiratory conduit 117 in such a way that when the ball 305 is connected to a medical stand, the expiratory conduit 117 is positioned below the inspiratory conduit 103. For example, but without limitation, the body 310 may be adapted to connect to any one or more of the locking clips disclosed in U.S. Patent Application Publication No. 2014/0236041 that is engageable with multiple tubes.

Figure 3B:
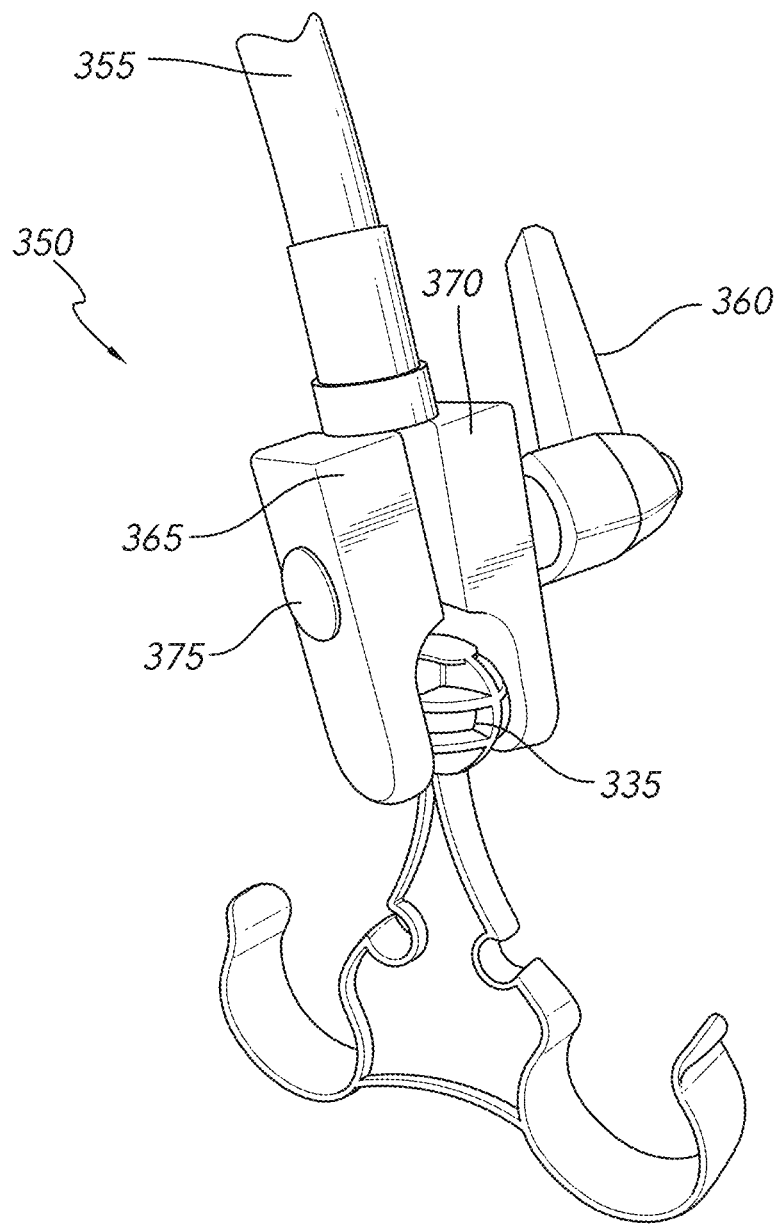
FIG. 3B is a diagram of a ball-holding end of a medical stand that may be attached to a connector for a respiratory assistance system that comprises a circuit hanger.
Figure 3C:
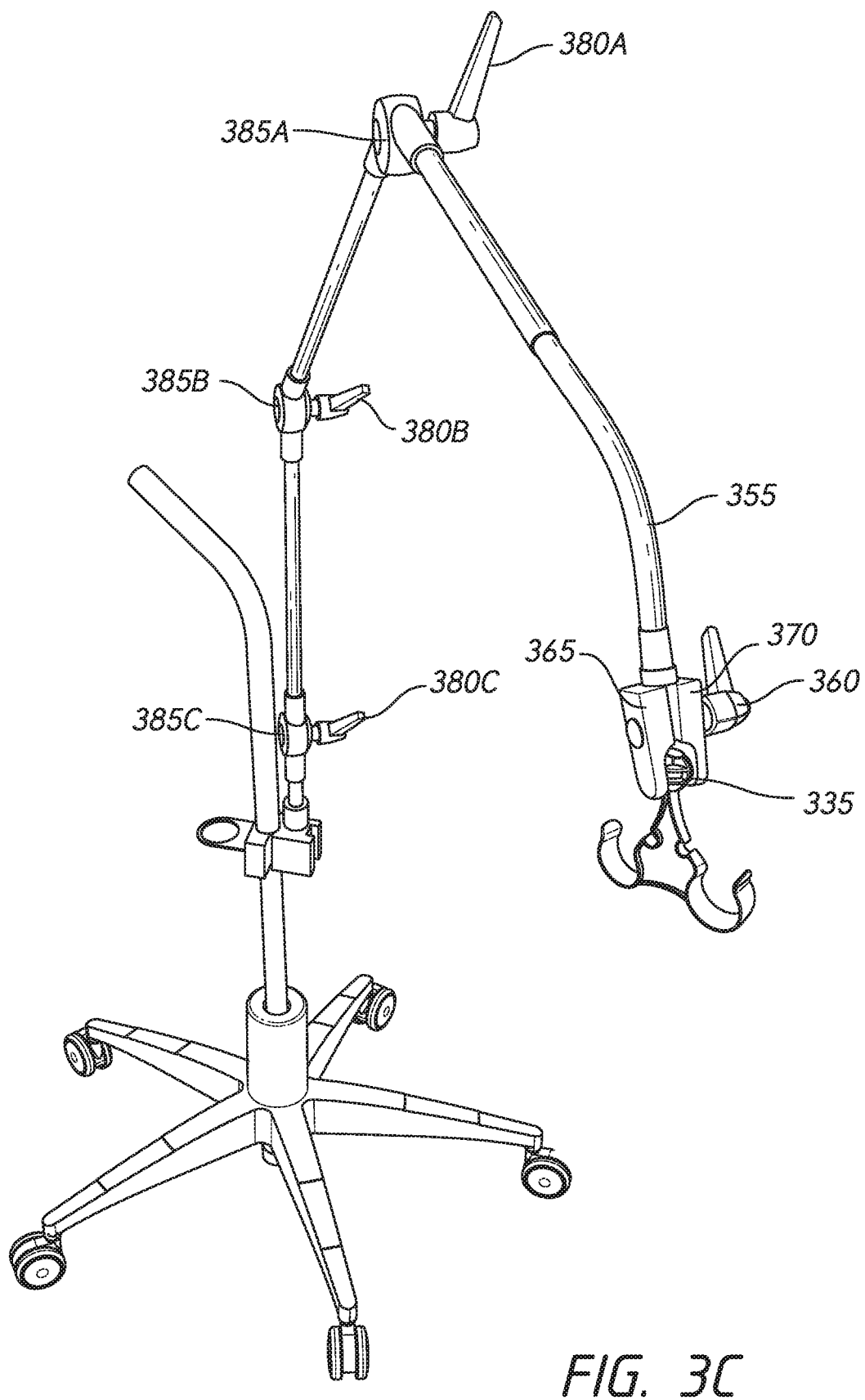
FIG. 3C is a diagram of a medical stand that may be attached to a connector for a respiratory assistance system that comprises a circuit hanger.

Medical Stand to Secure Ball (FIGS. 3B and 3C)

FIG. 3B is a diagram of a ball-holding end 350 of a medical stand that may be attached to a connector for a respiratory assistance system that comprises a circuit hanger. The ball-holding end 350 of the medical stand is attached to an arm 355. The arm 355 may be a flexible arm that allows the ball-holding end 350 to be positioned and oriented by a user.

The ball-holding end 350 has a first clamp 365 and a second clamp 370. The first clamp 365 and the second clamp 370 have a hole in which a screw 375 may be disposed. The screw 375 may be mated with a handle 360. The handle 360 may have threads such that rotating the handle in one direction will bring the first clamp 365 and a second clamp 370 closer together, while rotating the handle in another direction will bring the first clamp 365 and the second clamp 370 further apart. The connector may have a ball 335 that may be held within the jaws of the first clamp 365 and the second clamp 370. By bringing the first clamp 365 and the second clamp 370 closer together, the ball 335 and the connector may be held in a specific orientation or position. By bringing the first clamp 365 and the second clamp 370 further apart, the ball 335 may be loosened from the grip of the first clamp 365 and the second clamp 370 enough that the orientation or position of the ball 335 and the connector may be changed.

However, the ball-holding end 350 may not necessarily be configured to tighten or loosen so that the orientation or position of the connector may be changed. Instead, a different mechanism may be used to attach to, hold, or secure the ball 335 of the connector.

FIG. 3C is a diagram of a medical stand that may be attached to a connector for a respiratory assistance system that comprises a circuit hanger. It has a ball-holding end attached to the arm 355, with the ball-holding end having a first clamp 365 and a second clamp 370. A handle 360 is mated to a screw (not shown) running through the first clamp 365 and the second clamp 370. The first clamp 365 and the second clamp 370 securely hold the ball 335 of a connector.

The medical stand also has additional features which allow the orientation and positioning of the ball-holding end and, by extension, the ball 335 and connector, to be changed and fixed as desired. The arm of the medical stand may be articulated at various joints. For example, there is a handle 380A attached to a joint 385A. The handle 380A may be rotated in order to tighten or loosen the joint 385A. Loosening the joint 385A may allow the arm of the medical stand to be articulated at joint 385A. The arm of the stand may then be rotated into a desired orientation or position for the joint 385A to be tightened, after which the arm will be secured in its new desired orientation or position. Similarly, there may be a handle 380B for controlling a joint 385B, a handle 380C for controlling a joint 385C, and so forth.

Figure 4:
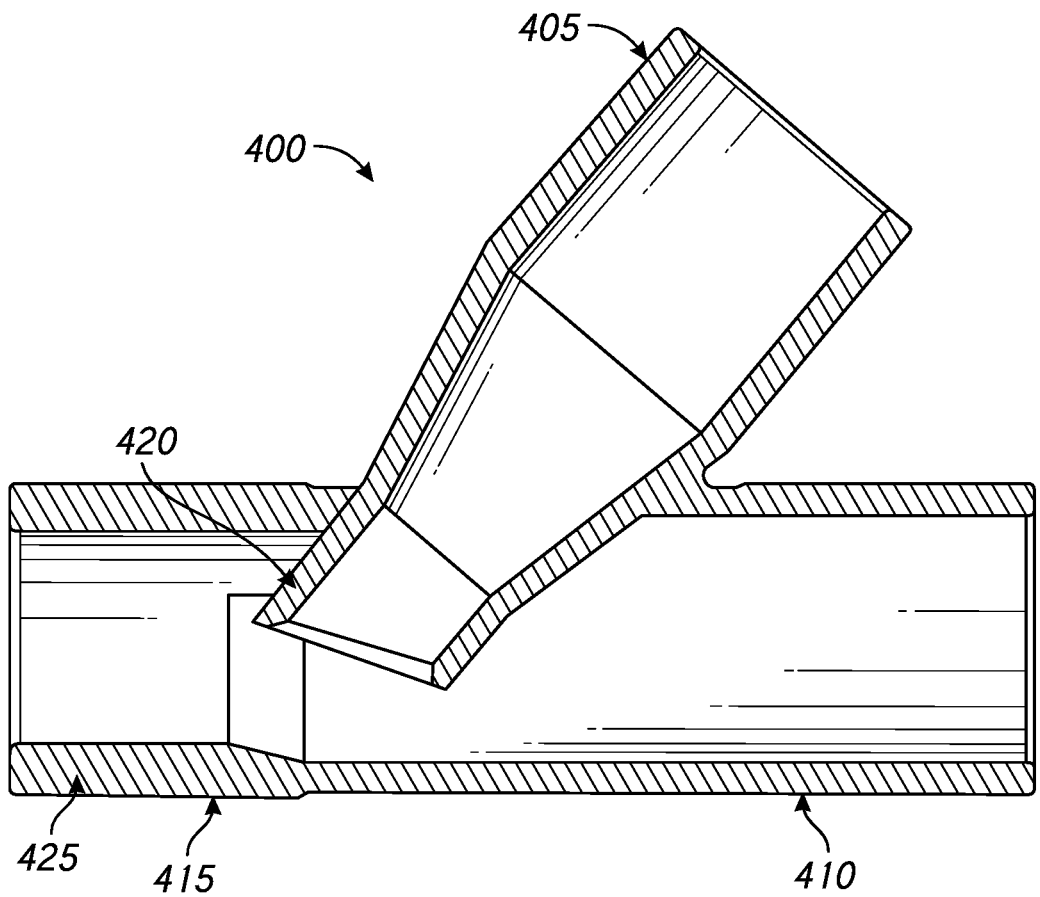
FIG. 4 is a diagram of a connector for a respiratory assistance system according to an example embodiment in which the connector comprises a coaxial wye-piece.

Coaxial Wye-Piece Connector (FIG. 4)

FIG. 4 illustrates a connector for the respiratory assistance system 100 according to a third example embodiment, where the connector includes a coaxial wye-piece 400.

The coaxial wye-piece 400 has a smooth inner wall surface, so that it has a similar resistance to flow as other wye-piece connectors, such as the wye-piece 113 shown in FIG. 1. The coaxial wye-piece 400 may be a single-use wye-piece or a reusable wye-piece. The coaxial wye-piece 400 may be configured to work with various types of conduits, such as smooth-bore conduits, in order to reduce the amount of condensate entering the inspiratory conduit 103 during invasive or non-invasive ventilation.

The coaxial wye-piece 400 has an inspiratory branch 405 that connects to, or interfaces with, the inspiratory conduit 103. Respiratory gases from the inspiratory conduit 103 flow into the coaxial wye-piece 400 through the inspiratory branch 405. The orientation of the inspiratory branch 405 directs respiratory gases from the inspiratory conduit 103 towards the patient 101. The respiratory gases flows towards a patient end 415 of the coaxial wye-piece 400, where it may travel through the patient interface 115 before being breathed in by the patient 101.

Once the patient 101 exhales, the exhaled gases may enter the coaxial wye-piece 400 through the patient end 415. The exhaled gas will flow towards an expiratory branch 410 of the coaxial wye-piece 400, which connects to, or interfaces with, the expiratory conduit 117. The coaxial wye-piece 400 provides a straight path from the patient end 415 to the expiratory branch 410. A lip or extension 420 prevents or obstructs condensate in the exhaled gas from entering the inspiratory branch 405 and the inspiratory conduit 103. This decreases the proportion of condensate that drains into the inspiratory conduit 103 regardless of the orientation or positioning of the inspiratory conduit 103 relative to the expiratory conduit 117. The condensate is directed towards the expiratory conduit 117.

The diameter of the inspiratory branch 405 narrows from the conduit interface end of inspiratory branch 405 to the lip 420. The narrowing of the diameter near the lip 420 causes the respiratory gas that flows into the coaxial wye-piece 400 through the inspiratory branch 405 to move faster as the diameter narrows based on Pouseuille's Law. This increased speed of gas flow may discourage or prevent condensate from traveling against the flow direction and entering the inspiratory branch 405, thereby keeping condensate out of the attached inspiratory conduit 103.

A solid wall 425 on the patient end 415 of the coaxial wye-piece 400 has a dual taper design, so that the patient end 415 may act as a female or male connector. There is a taper on the outside surface of the solid wall 425 so that the patient end 415 may act as a male connector. For example, the patient end 415 may be configured to have a 22 mm male connection to fit into a standard 22 mm female taper. There is a taper on the inner surface of the solid wall 425 so that the patient end 415 may act as a female connector. For example, the patient end 415 may be configured to have a 15 mm female connection for connecting to a 15 mm male taper of a trachea mount, the patient interface 115, and so forth. Other embodiments of the coaxial wye-piece 400 for which the wall of the patient end 415 is not a solid wall, such as the solid wall 425, but still maintains the dual taper design is described below with regard to FIGS. 5A and 5B.

The solid wall 425 may be further configured or designed to meet desired commercial goals. Making the solid wall 425 as thin as possible may aid in the manufacturing of the wye-piece 400. For example, if the wye-piece 400 is injection moulded then having the solid wall 425 as thin as possible will reduce the time needed for the wye-piece 400 to cool and improve the moulding stability of tapered portions of the solid wall 425. A thin embodiment of the solid wall 425 will also reduce the amount of material (such as plastic) needed to produce the wye-piece 400, which results in lower unit costs and shorter manufacturing times.

The coaxial wye-piece 400 drains condensate to the expiratory branch 410 regardless of the orientation of the coaxial wye-piece 400. In a scenario where the orientation of the coaxial wye-piece 400 has the inspiratory branch 405 pointed downwards towards the ground with no flow coming from the inspiratory branch 405, it will be unlikely that condensate flows into the inspiratory branch 405. The lip 420 prevents condensate from entering the inspiratory branch 405 in such an orientation. In more common scenarios where the inspiratory branch 405 is not pointed downwards, any condensate that splashes into the inspiratory branch 405 falls back down into the straight flow path between the patient end 415 and the expiratory branch 410. The design of the coaxial wye-piece 400 allows condensate to be kept out of the inspiratory conduit 103 for seven days or more, in comparison to some wye-piece designs in which condensate may be found in the inspiratory conduit 103 within six hours of use. Furthermore, the design of the coaxial wye-piece 400 provides these benefits without greatly increasing the resistance to flow of respiratory gases passing through any portion of the wye-piece 400. In particular, there may be little change to the resistance to flow between the patient end 415 and the expiratory branch 410 in comparison to other wye-piece designs. The flow path between the patient end 415 and the expiratory branch 410 is a straight path in which the lip 420 creates a relatively minor obstruction to flow.

By being able to function in different orientations, the coaxial wye-piece 400 allows the respiratory assistance system 100 to be simple to set up and use effectively by taking the orientation of the coaxial wye-piece 400 out of consideration during setup. Thus, the coaxial wye-piece 400 may be particularly useful in reusable respiratory assistance systems, which may have breathing circuits that are not preassembled and more prone to user error in circuit setup. The coaxial wye-piece 400 may also be particularly suitable for use at home.

Figure 5A:
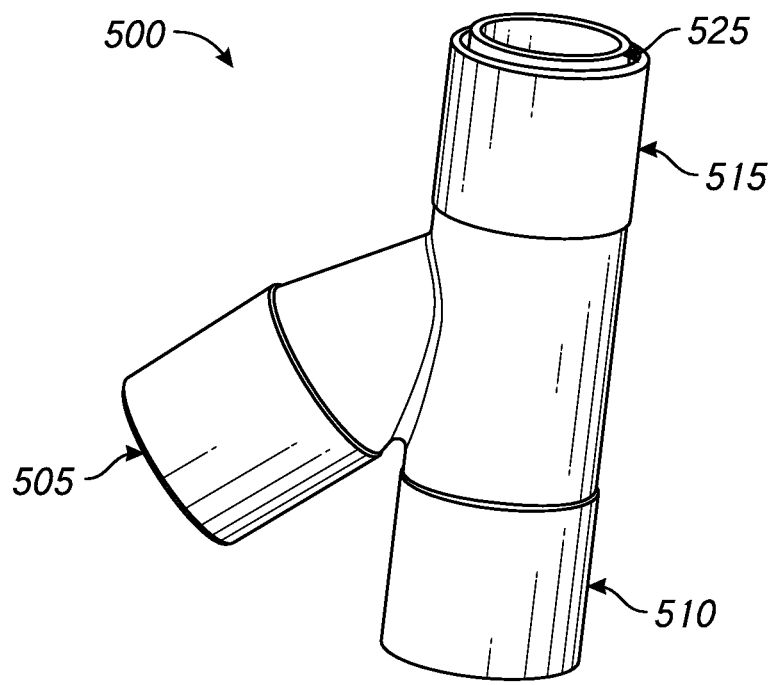
FIG. 5A is a diagram illustrating a perspective side view of a connector for a respiratory assistance system according to an example embodiment in which the connector comprises a coaxial wye-piece.
Figure 5B:
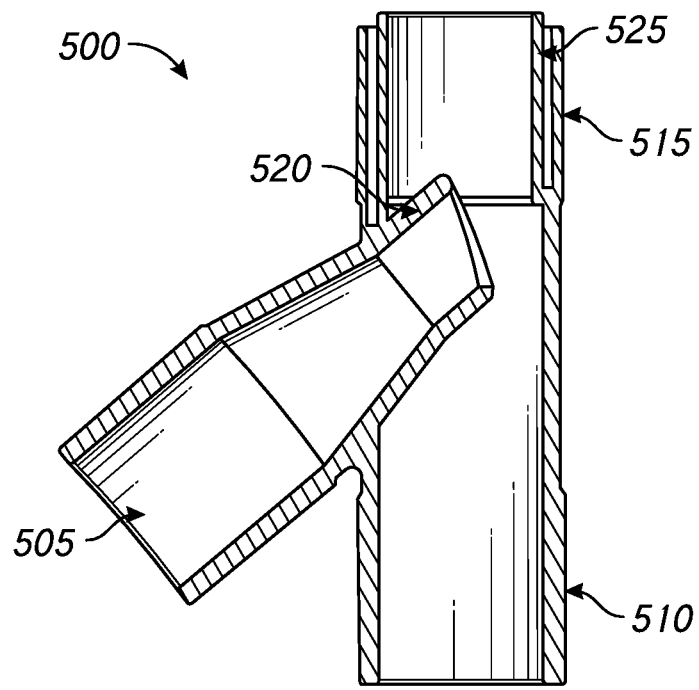
FIG. 5B is a diagram illustrating a side cut-away view of a connector for a respiratory assistance system according to the example embodiment of FIG. 5A in which the connector comprises a coaxial wye-piece.

Coaxial Wye-Piece Connector With Gap (FIGS. 5A and 5B)

FIGS. 5A and 5B both show a connector for the respiratory assistance system 100 according to an example embodiment where the connector includes a coaxial wye-piece 500. FIG. 5A illustrates a perspective view of the coaxial wye-piece 500 while FIG. 5B illustrates a side cutaway view of the same coaxial wye-piece 500.

The coaxial wye-piece 500 is very similar in design and operation to the coaxial wye-piece 400 described above in reference to FIG. 4. For example, the coaxial wye-piece 500 also has an inspiratory branch 505, an expiratory branch 510, and a patient end 515. Observable in FIG. 5B is a lip 520 which is similar to the lip 420 shown in the embodiment of FIG. 4. The main difference between the embodiments is that the coaxial wye-piece 500 has a wall gap 525, whereas the coaxial wye-piece 400 from FIG. 4 has the solid wall 425. Instead of the solid wall 425 between the inner surface and the outer surface of the patient end 415 of the coaxial wye-piece 400, the coaxial wye-piece 500 has the wall gap 525 that separates the inner surface and the outer surface of the patient end 515.

Normally in a reusable circuit, the presence of the wall gap 525 may act as a dirt trap which may make the wye-piece connector difficult to clean for reuse. However, this drawback of the wall gap 525 is mitigated in single-use applications. The wye-piece 500 is generally a single-use coaxial wye-piece connector with the wall gap 525, such that cleaning the wall gap 525 is unnecessary.

The wall gap 525 may have a thickness defined in part by the distance between the outer surface and the inner surface of the patient end 515. If the patient end 515 is configured to have a dual taper design that supports a 15 mm female connection and a 22 mm male connection, then the wall gap 525 may have a thickness that is associated with the distance between the 15 mm female connection and the 22 mm male connection. Thus, the patient end 515 having a dual taper design does not exclude the possibility of having the wall gap 525.

If the patient end 515 is has a solid wall, then more material (such as plastic) would be used in comparison to having the wall gap 525 in the patient end 515, which reduces the material used by the volume of the cylindrical shell defined by the thickness of the wall gap 525. Thus, the wall gap 525 may reduce the amount of material needed to manufacture the coaxial wye-piece 500 as well as reduce the manufacturing time of the coaxial wye-piece 500 since the thinner walls of the patient end 515 would take less time to cool. Otherwise, the wye-piece 500 maintains many of the features described of the wye-piece 400 shown in FIG. 4. The wye-piece 500 has a similar inspiratory branch and expiratory branch with tapers at the end of both. The patient end 515 of the wye-piece 500 may preserve the dual taper design such that the patient end 515 may act as either a male connector or a female connector. Note that wall gap 525 is a feature that may be present in combination with any of the embodiments of connectors disclosed herein including the embodiment of wye-piece 200 shown in FIG. 2. As further examples, it may also be applied in combination with the embodiments shown in FIGS. 4, 6, 7A, 7B, 9, 10, 11, and 12.

Wye-Piece Geometry (FIGS. 6, 7A, 7B, 8A, 8B, and 9)

Figure 6:
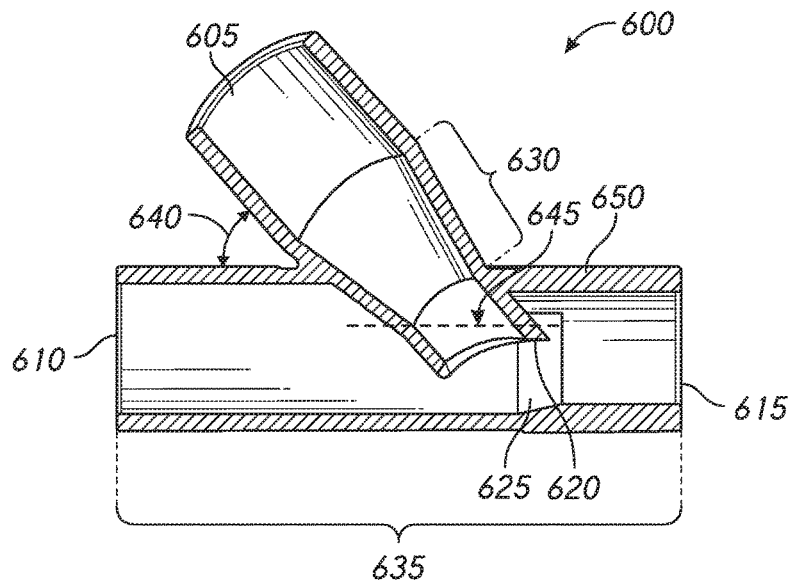
FIG. 6 is a diagram illustrating a cut-away view of the geometry and positioning of features of a connector for a respiratory assistance system in which the connector comprises a coaxial wye-piece.

FIG. 6 is a cutaway view illustrating the geometry and positioning of features for a connector in the respiratory assistance system 100 that includes a coaxial wye-piece 600.

The coaxial wye-piece 600 may be the same embodiment as the coaxial wye-piece 400 shown in FIG. 4. The wye-piece 600 may be opaque or it may be transparent to some degree in order to show the internal construction of the wye-piece 600. In some embodiments, the wye-piece 600 may have a certain colour and/or degree of transparency to indicate whether it is a single-use wye-piece or a reusable wye-piece. The coaxial wye-piece 600 has some similar features to the coaxial wye-piece 400, including an inspiratory branch 605, an expiratory branch 610, a patient end 615, and a lip 620. However, there may be minor changes with regards to the spacing, angle, or length of the ports and branches.

A length 630 is the length between the tapered end of the inspiratory branch 605 and the intersection of the main body of the wye-piece 600. Over the length 630, the inspiratory branch 605 narrows. This configuration speeds up the flow of respiratory gas moving towards the patient end 615. However, in some embodiments, the inspiratory branch 605 does not narrow. In various embodiments, the length 630 may be altered to serve specific design goals. In various embodiments, the length 630 may be increased in order to provide more space for connectors.

An angle 640 is the angle between the inspiratory branch 605 and the expiratory branch 610. In various embodiments, the angle 640 may be in the range of between 0 and 180 degrees. In various embodiments, the angle 640 may be in the range of between 0 and 90 degrees. For practical reasons, the angle 640 is normally within the range of 0 and 90 degrees, such that gas flowing into the inspiratory branch 605 is naturally directed towards the patient end 615. In some embodiments, the angle 640 is between 30 and 60 degrees. In some embodiments, the angle 640 is between 40 and 50 degrees. In some embodiments, the angle 640 is 45 degrees.

A length 635 is the length between the dual-tapered patient end 615 and the expiratory branch 610. In various embodiments, the length 635 may be altered to serve specific design purposes. In various embodiments, the length 635 is at least the distance from the lip-end of the inspiratory branch 605 to the patient end 615. In various embodiments, including the one shown in FIG. 6, the length 635 is significantly greater (by a factor of two in the illustration) than the distance from the lip-end of the inspiratory branch 605 to the patient end 615, in order to accommodate at least any taper at the end of the expiratory branch 610. This allows the expiratory branch 610 to be connected to other objects in the respiratory assistance system 100, such as the expiratory conduit 117. In some embodiments, the length 635 may be altered in order to accommodate or fit an MDI port or other feature, such as a pressure port. Further discussion on MDI port placement is provided below in reference to FIG. 7A.

A dotted line 645 shows how the tip or end of the inspiratory branch 605 near the lip 620 may be trimmed. In various embodiments, the tip of the inspiratory branch 605 may be trimmed in order to reduce resistance to flow from the patient end 615 toward the expiratory branch 610, as well as material usage and cost, in comparison to having an extended tip. The shortened tip can still prevent condensate from entering the inspiratory branch 605 since the lip 620 will still be present. The shortened tip will also still direct respiratory gas flow towards the patient end 615. A minimum amount of tip is desirable in order to direct a flow of gases to the patient 101.

There is an inner diameter change 625 in the inner surface of the body of the wye-piece 600 between the expiratory branch 610 and the patient end 615. In some embodiments, the inner diameter change 625 is not present. The inner diameter change 625 accommodates a smaller inner surface diameter at the patient end 615 due to the taper needed for the patient end 615 to serve as a 15 mm female connector.

In some embodiments, the dual taper of the patient end 615 does not conform to the standard 15 mm female connection. The patient end 615 may have a taper for any size female connection, such as 13 mm, 17 mm, 19 mm, and so forth. The inner diameter change 625 may be different to accommodate the taper or the inner surface diameter of the patient end 615. The inner diameter change 625 may be a smooth inner transition in diameter from the expiratory branch 610 and the patient end 615. A stepwise, or other similarly abrupt, change in diameter may affect the cleaning and flow characteristics of the wye-piece 600. The wye-piece 600, with the inner diameter change 625 having a smooth transition, has a resistance to flow that is very similar to a wye-piece with no inner diameter change.

To the implement inner diameter change 625, an upper wall 650 of the wye-piece 600 that is near the lip 620 can be straight rather than angled in order to aid in manufacturing. In some embodiments, the upper wall 650 will be straight. In other embodiments, the upper wall 650 will be angled to contribute to the inner diameter change 625. If the upper wall 650 is straight, then the inner diameter change 625 may not be attributed to a change in the upper wall 650, but rather a change in the wall thickness of the wall on the opposite side of the upper wall 650. This can be seen in FIG. 6 in the lower wall directly below the inner diameter change 625.

Changing the diameter of the inspiratory conduit 103, which may be a smooth-bore conduit, may also be reflected in a change in the diameter of the inspiratory branch 605 and may affect the function and design of the wye-piece 600. For instance, a decrease in the diameter of the smooth-bore conduit may be reflected in the inspiratory branch 605 in a variety of ways. For example, there may be an aggressive taper at the end of the inspiratory branch 605 in order to fit the decreased smooth-bore conduitdiameter. The respiratory gases flowing through the smooth-bore conduitwill slow down once it enters the inspiratory branch 605. The respiratory gases flow may speed up again as the diameter of the inspiratory branch 605 narrows. As another example, the inner diameter of the inspiratory branch 605 may be decreased in order to match the decreased smooth-bore conduitdiameter. This may be accomplished by reducing the outer diameter of the inspiratory branch 605 and/or by increasing the thickness of the walls of the inspiratory branch 605. The result will be faster respiratory gas flow through the smooth-bore conduit and the inspiratory branch 605 due to the decreased diameter.

Thus, the length 630, the length 635, the angle 640, the length of the tip of inspiratory branch 605, the diameter of inspiratory branch 605, and the inner diameter change 625 all may be changed independently or in consideration of one another in order to facilitate a specific design purpose. For example, if directing respiratory gas flow from the inspiratory branch 605 towards the patient end 615 is a priority, then the angle 640 may be chosen to be smaller, and the tip of the inspiratory branch 605 may be chosen to be longer. All of these changeable features described here in connection to FIG. 6 may be applied to any other embodiment of a coaxial wye-piece described herein, including but not limited to, the embodiments shown in FIGS. 4, 5A, 5B, 9-12.

Figure 7A:
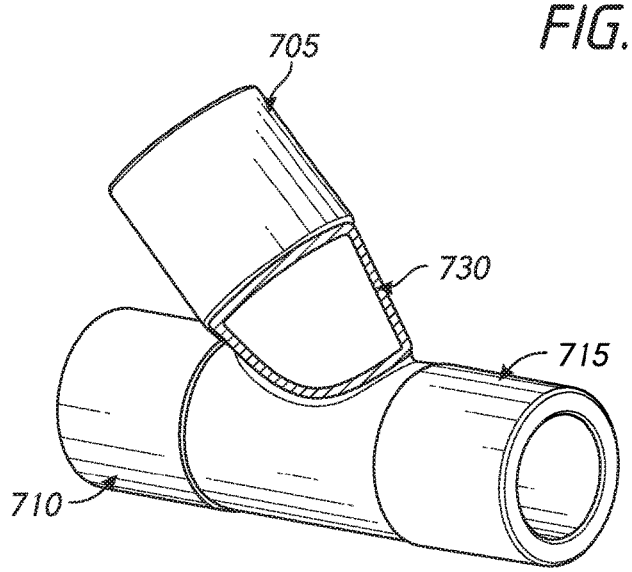
FIG. 7A is a diagram of where an MDI port may be located on a connector in a respiratory assistance system in which the connector comprises a coaxial wye-piece.

FIG. 7A illustrates an embodiment where an MDI port may be located on a coaxial wye-piece connector in the respiratory assistance system 100. The coaxial wye-piece connector shown has an inspiratory branch 705, an expiratory branch 710, and a patient end 715. In some cases, it may be desirable for the coaxial wye-piece connector to have an MDI port. However, such an MDI port should generally not be located on the tapers towards the ends of inspiratory branch 705, expiratory branch 710, and patient end 715. Locating an MDI port on a taper would impair the taper and interfere with the ability of that end of the wye-piece to serve as a connector. The MDI port should also be associated with inspiratory gases, such that any medication delivered through the MDI port is delivered to the patient during inspiration. Thus, the MDI port may be positioned anywhere on the inspiratory branch 705 of the wye-piece that does not form the taper of the inspiratory branch 705. This permissible area of placement is shown in FIG. 7A as section 730 of the inspiratory branch 705.

Figure 7B:
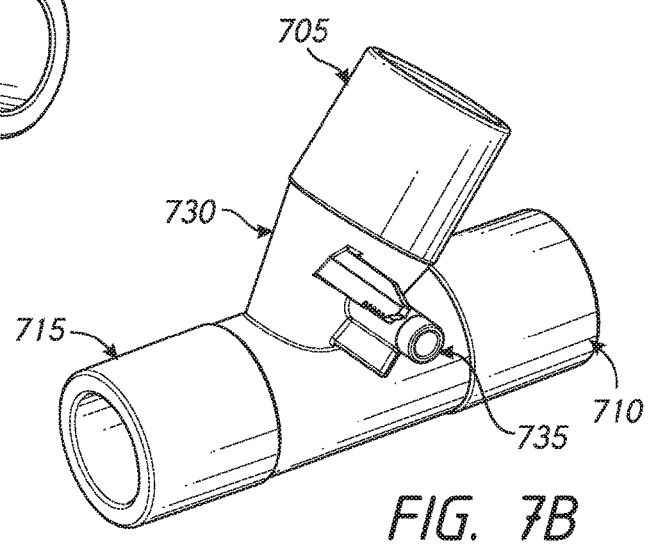
FIG. 7B is a diagram illustrating a connector for a respiratory assistance according to an example embodiment in which the connector comprises a coaxial wye-piece with an MDI port.

FIG. 7B is a diagram illustrating a connector for a respiratory assistance according to an example embodiment in which the connector comprises a coaxial wye-piece with an MDI port 735. The figure is similar to FIG. 7A, with the connector having the same inspiratory branch 705, an expiratory branch 710, and a patient end 715. Inspiratory branch 705 has an MDI port 735 located in section 730 of the inspiratory branch 705. Note that MDI port 735 may actually be located anywhere within section 730.

Figure 8B:
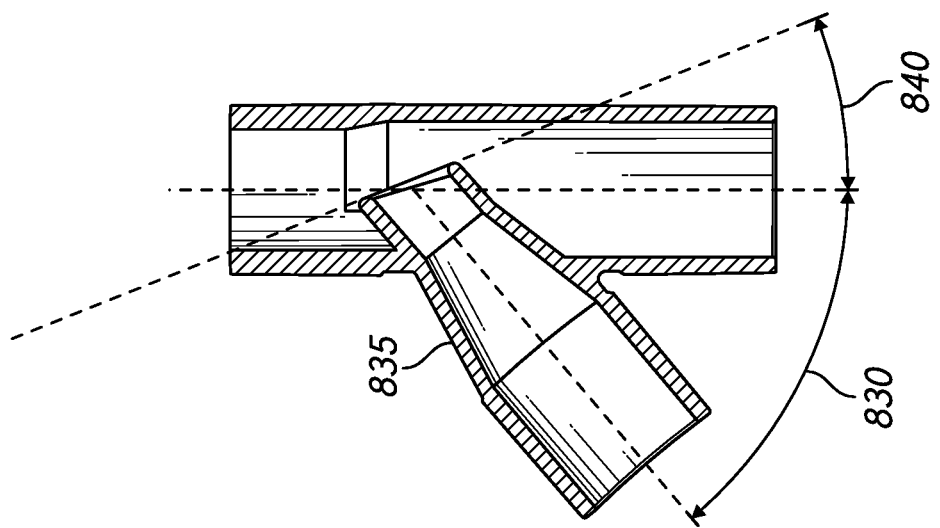
FIG. 8B is a diagram illustrating a cross-section view of the dimensions and angles of a connector for a respiratory assistance system in which the connector comprises a coaxial wye-piece.
Figure 8A:
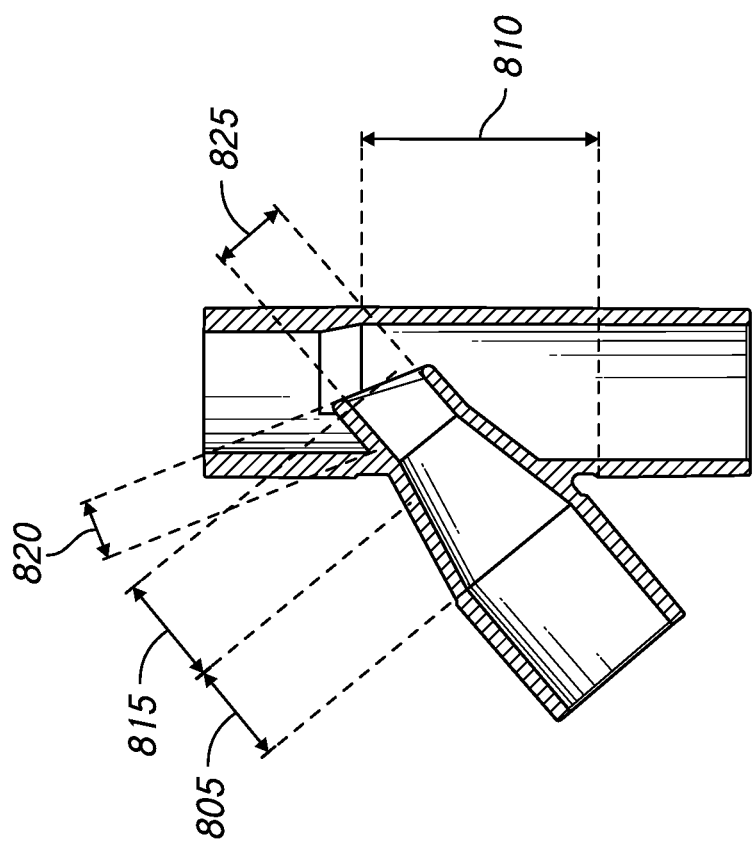
FIG. 8A is a diagram illustrating a cross-section view of the dimensions and lengths of a connector for a respiratory assistance system in which the connector comprises a coaxial wye-piece.

FIGS. 8A and 8B are cross-sectional views that further show the geometry and dimensions for a connector in the respiratory assistance system 100 that comprises a coaxial wye-piece.

In FIG. 8A, representations of the lengths and distances of various features are shown.

A length 805 represents the distance between where the inspiratory branch begins to narrow and where the inspiratory branch connects to the body of the wye-piece. The length 805 may be measured along the axis of the inspiratory branch. Changing the length 805 may alter the rate at which the inspiratory gas flow speed changes as the inspiratory branch narrows.

For the portion of wye-piece between the patient end and the expiratory branch, a length 810 represents the horizontal distance between where the inspiratory branch joins the wye-piece to the inner diameter change. Changing the length 810 may alter the resistance to flow of the wye-piece.

A length 815 represents the distance between where the inspiratory branch connects to the body of the wye-piece to the tip of the inspiratory branch. The length 815 may be measured along the axis of the inspiratory branch. Changing the length 815 may alter the resistance to flow of the wye-piece. The length 815 may be shortened such that the tip of the inspiratory branch still has a lip, allowing for condensate to still be obstructed from entering the inspiratory branch. One side of the inspiratory branch may be shortened so that the tip of the inspiratory branch still has a lip, as shown in FIG. 6 in which the inspiratory branch may be shortened up to the dotted-line 645.

A length 820 represents the distance from the upper wall to the lip of the tip of the inspiratory branch. The length 820 may be measured along the outer surface of the tip of the inspiratory branch. Changing the length 820 may alter the size of the lip.

A length 825 represents the inner surface diameter of the tip of the inspiratory branch. The length 825 may be changed to affect the inspiratory gas flow speed being delivered towards the patient end. A smaller diameter will result in higher flow speed, and increased resistance to flow, while a larger diameter will result in lower flow speed, and decreased resistance to flow.

The table below provides approximate dimensions of the lengths illustrated in FIG. 8A.

| Dimensions of FIG. 8A | | |
| --- | --- | --- |
| | Illustrated Dimension | Alternative Dimensions |
| Length 805 | 13 mm | 10-25 mm |
| Length 810 | 31 mm | 20-40 mm |
| Length 815 | 16 mm | 5-20 mm |
| Length 820 | 8 mm | 4-10 mm |
| Length 825 | 10 mm | 5-15 mm |

In FIG. 8B, representations of the angles of various features are shown.

An angle 830 is the angle between the axis of the inspiratory branch and the axis of the expiratory branch. Changing the angle 830 may alter how the inspiratory gas flowing through inspiratory branch is directed towards the patient end. At higher values for the angle 830, the inspiratory gas becomes less directed towards the patient end and increasingly directed towards the opposing wall facing the tip of the inspiratory branch.

An angle 835 is the angle between the narrowing portion of the inspiratory branch and the axis of the inspiratory branch. Changing the angle 835 may alter the rate of change of the narrowing of the inspiratory branch. At higher values for the angle 835, the inspiratory branch may narrow quickly. This may result in the flow speed of inspiratory gases increasing more rapidly over the narrowing portion as opposed to lower values for the angle 835.

An angle 840 is the angle between the tip of the inspiratory branch and the axis of the expiratory branch. Changing the angle 840 may alter the resistance to flow of the wye-piece as well as how inspiratory gas is directed towards the patient end. For greater values of the angle 840, there may be greater resistance to flow. However, inspiratory gas is better directed towards the patient end. For lower values of the angle 840, there may be less resistance to flow but inspiratory gas is not as well directed towards the patient end. The angle 840 may be chosen in order to achieve the desired features of the wye-piece and strike the right balance between resistance to flow and directing gas towards the patient end.

The table below provides approximate dimensions of the angles illustrated in FIG. 8B.

| Angles of FIG. 8B | | |
| --- | --- | --- |
| | Illustrated Dimension | Alternative Dimensions |
| Angle 830 | 50° | 50-90° |
| Angle 835 | 12° | 10-90° |
| Angle 840 | 20° | 0-35° |

Thus, the dimensions of the various lengths described in reference to FIG. 8A, the dimensions of the various angles described in reference to FIG. 8B, and the dimensions of the various features described in reference to FIG. 6 (which include the length 630, the length 635, the angle 640, the length of the tip of the inspiratory branch 605, the diameter of the inspiratory branch 605, and the inner diameter change 625) may all be chosen in order to facilitate the desired functionality of the wye-piece. The desired wye-piece connector may be designed to have at least one of a specific resistance to flow (especially with regards to the expiratory branch), inhibit condensate movement into the inspiratory branch to a certain degree, minimize carbon dioxide build-up, have an MDI port for the patient's convenience, and/or meet a certain degree of usability (such as by eliminating the need for a user to set up the wye-piece in a specific orientation).

Figure 9:
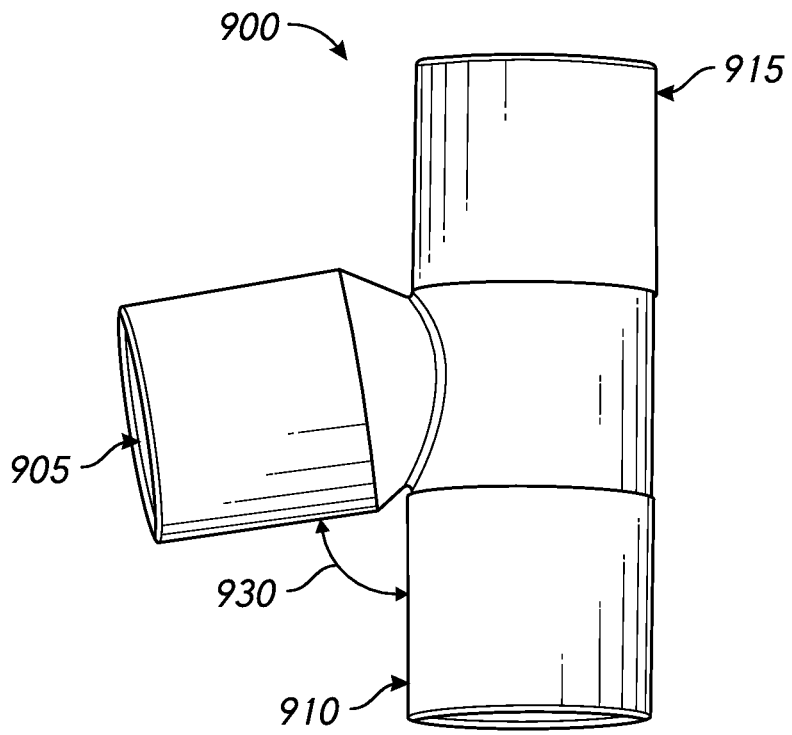
FIG. 9 is a diagram of a connector for a respiratory assistance system according to an example embodiment in which the connector comprises a coaxial wye-piece.

FIG. 9 illustrates a connector for the respiratory assistance system 100 according to another example embodiment, where the connector comprises a coaxial wye-piece 900.

The coaxial wye-piece 900 has an inspiratory branch 905, an expiratory branch 910, and a patient end 915. An angle 930 between the inspiratory branch 905 and the expiratory branch 910 is greater than the angles in some of the other embodiments shown in the figures, such as the embodiment shown in FIG. 4. The larger angle 930 makes inspiratory gas from the inspiratory branch 905 less directed towards the patient end 915 of the wye-piece 900. For example, the inspiratory gas retains a significant horizontal momentum that may carry it into the wall of the wye-piece 900 directly opposing the tip of the inspiratory branch 905 (not shown).

The inspiratory branch 905 shown is also shorter in length than the inspiratory branch of the embodiment in FIG. 4. The taper on the end of the inspiratory branch 905 takes up most of the length of the inspiratory branch 905. The length of the narrowing portion of the inspiratory branch 905 is very short.

Figure 10:
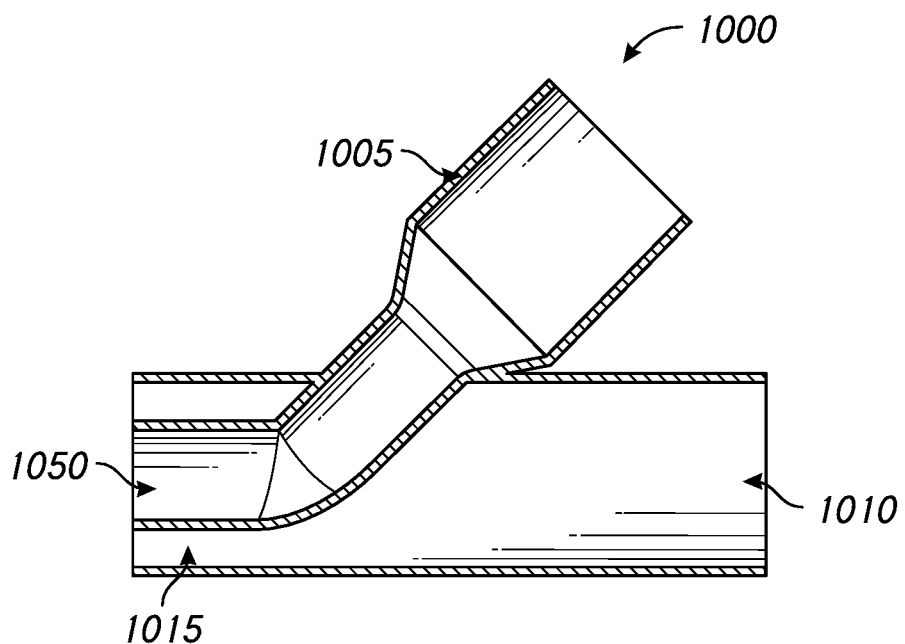
FIG. 10 is a diagram of a connector for a respiratory assistance system according to an example embodiment in which the connector comprises a coaxial wye-piece.
Figure 11:
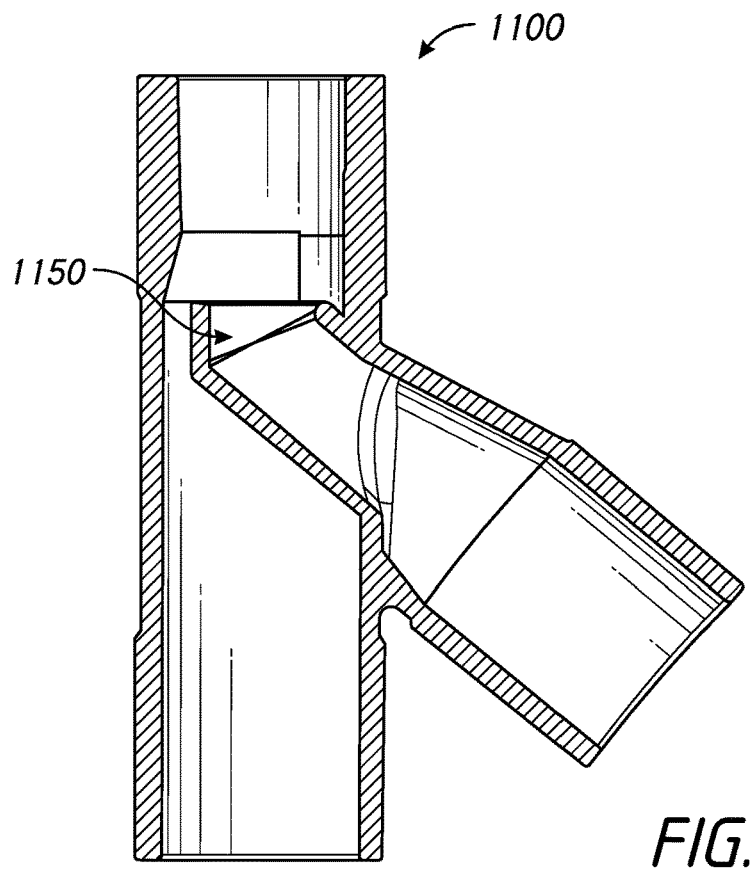
FIG. 11 is a diagram of a connector for a respiratory assistance system according to an example embodiment in which the connector comprises a coaxial wye-piece.
Figure 12:
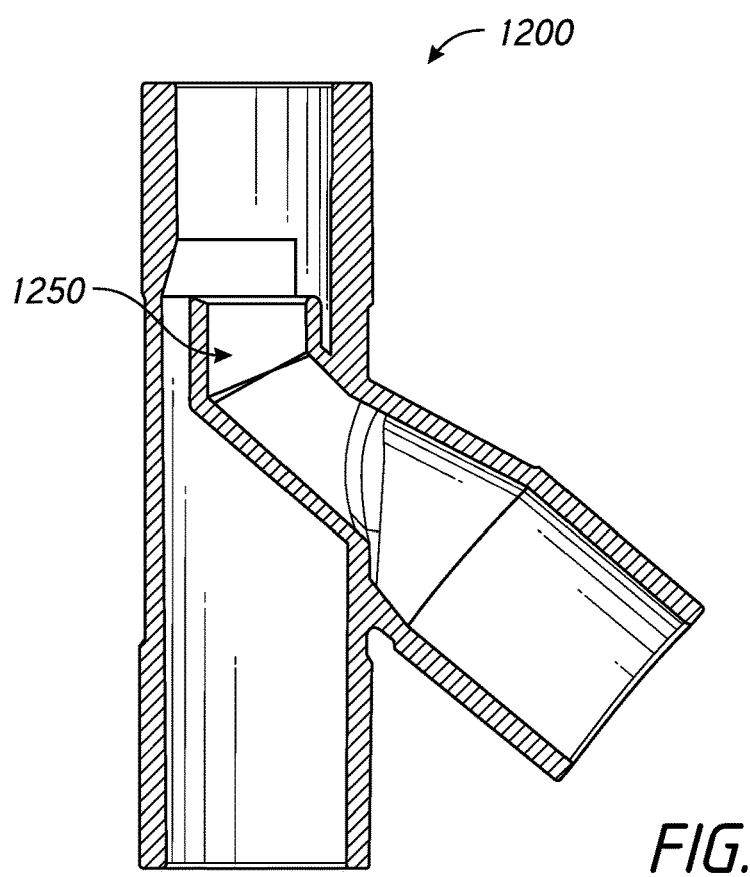
FIG. 12 is a diagram of a connector for a respiratory assistance system according to an example embodiment in which the connector comprises a coaxial wye-piece.

Coaxial Wye-Piece With Inner Coaxial Tube (FIGS. 10, 11, and 12)

FIG. 10 illustrates a connector for the respiratory assistance system 100 according to an example embodiment, where the connector includes a coaxial wye-piece 1000.

Coaxial wye-piece 1000 has an inspiratory branch 1005, an expiratory branch 1010, and a patient end 1015. There is also an inner coaxial inspiratory tube 1050 which runs the length of the patient end 1015 of the wye-piece 1000. Inner coaxial inspiratory tube 1050 is an extension of inspiratory branch 1005 that extends from the inspiratory branch 1005 into the wye-piece 1000. Inner coaxial inspiratory tube 1050 helps to ensure that condensate is directed away from the inspiratory gas flow because inner coaxial inspiratory tube 1050 is pointed towards patient interface 115. The interface connector of patient interface 115 does not contact the inner coaxial inspiratory tube 1050. The interface connector would connect to patient end 1015 so that inspiratory and expiratory gas may pass through the interface connector.

However, the inner coaxial inspiratory tube 1050 may have a negative impact on resistance to flow as there may only be a small amount of available space within the 15 mm taper of the patient end 1015 to fit a completely coaxial tube. The presence of the inner coaxial inspiratory tube 1050 may also restrict the expiratory flow towards the expiratory branch since it takes up a significant portion of the cross-section of the wye-piece 1000.

FIG. 11 illustrates a connector for the respiratory assistance system 100 according to an example embodiment, where the connector comprises a coaxial wye-piece 1100.

The coaxial wye-piece 1100 has an internal coaxial tube 1150 that terminates before the connection point with the interface at the patient end. The internal coaxial tube 1150 has a relatively short lip. The internal coaxial tube 1150 takes up a significant portion of the cross section of the flow path towards the expiratory branch, which may be a factor in condensate entering the inspiratory branch under certain conditions.

FIG. 12 illustrates a connector for the respiratory assistance system 100 according to an eighth example embodiment, where the connector comprises a coaxial wye-piece 1200.

The coaxial wye-piece 1200 has an internal coaxial tube 1250 that also terminates before the connection point with the interface at the patient end. The internal coaxial tube 1250 has a relatively longer lip than the lip of the internal coaxial tube 1150 shown in FIG. 11. Like in FIG. 11, here the internal coaxial tube 1250 takes up a significant portion of the cross section of the flow path towards the expiratory branch, which may be a factor in condensate entering the inspiratory branch under certain conditions.

Additional Description

It should be understood that any examples used in this description are in no way limiting, but merely illustrative of possible embodiments for purposes of clarification. Unless the context clearly requires otherwise, throughout this description and the claims that follow, the words "comprise", "comprising", and the like, are to be construed in an inclusive sense as opposed to an exclusive or exhaustive sense, that is to say, in the sense of "including, but not limited to".

Reference to any prior art in this description is not, and should not be taken as, an acknowledgement or any form of suggestion that the prior art referenced forms part of the common general knowledge in any relevant field of endeavour in any country in the world.

The present invention may be said broadly to consist in the parts, elements, and features referred to or indicated in this description and the claims that follow, individually or collectively, in any or all combinations of two or more of said parts, elements, or features. Where reference is made to integers or components having known equivalents thereof, those equivalents are herein incorporated as if individually set forth.

It should be noted that various modifications to the embodiments disclosed herein will be apparent to those skilled in the art. Such modifications may be made without departing from the spirit and scope of the present invention and without diminishing its attendant advantages. For instance, various components may be repositioned or reshaped as desired. It is therefore intended that such modifications be included within the scope of the invention. Moreover, not all of the features, aspects, and advantages disclosed herein are necessarily required to practice the present invention. Accordingly, the scope of the present invention is intended to be defined only by the claims that follow.

What is claimed is:

1. A wye-piece connector configured to be used in a respiratory assistance system, the wye-piece connector comprising:
   an inspiratory branch including an inspiratory conduit port and a meter-dosed inhaler (MDI) port;
   an expiratory branch including an expiratory conduit port;
   a patient end including a patient interface port; and a body comprising the inspiratory branch, the expiratory branch, and the patient end, wherein the body is formed by a first fluid passageway between the inspiratory conduit port and the patient interface port and a second fluid passageway between the expiratory conduit port and the patient interface port;
   wherein the inspiratory branch further comprises a tip that extends inwardly from an inner surface of the second fluid passageway into the second fluid passageway,
   the tip comprising an inspiratory branch end, the inspiratory branch end being at an angle relative to a patient interface port end such that the inspiratory branch end is oblique to a longitudinal axis extending through the patient interface port and the expiratory conduit port,
   wherein the MDI port is positioned between the inspiratory conduit port and the tip, and wherein the MDI port is located on a section of the inspiratory branch with a tapered inner diameter and a tapered outer diameter;
wherein the tip of the inspiratory branch comprises a lip, the lip configured to obstruct or impede condensate from entering into the inspiratory branch.

2. The wye-piece connector of claim 1, wherein the inspiratory conduit port is located on a conduit end of the inspiratory branch.

3. The wye-piece connector of claim 1, wherein the second fluid passageway comprises a change in an inner diameter of the second fluid passageway.

4. The wye-piece connector of claim 1, wherein the patient interface port is located on a free end of the patient end.

5. The wye-piece connector of claim 1, wherein the wye-piece connector is opaque.

6. The wye-piece connector of claim 1, wherein the wye-piece connector is transparent.

7. The wye-piece connector of claim 1, wherein the wye-piece connector is configured to direct flow from the inspiratory branch towards the patient end.

8. The wye-piece connector of claim 1, wherein the wye-piece connector comprises an angle between an axis of the inspiratory branch and an axis of the expiratory branch.

9. The wye-piece connector of claim 1, wherein the lip is located closer to the patient interface port than to the expiratory conduit port.

10. The wye-piece connector of claim 1, wherein the expiratory conduit port is coaxial with the patient interface port.

11. A system comprising:
an inspiratory conduit;
an expiratory conduit; and
the wye-piece connector of claim 1, wherein the inspiratory conduit port is configured to be removably connected to the inspiratory conduit and the expiratory conduit port is configured to be removably connected to the expiratory conduit.

12. The wye-piece connector of claim 1, wherein the tip is angled away from the patient interface port end.

13. The wye-piece connector of claim 2, wherein the inspiratory branch is configured to allow an inspiratory gas to flow within the inspiratory branch from the conduit end of the inspiratory branch to the tip of the inspiratory branch such that the inspiratory gas flow impedes condensate from entering into the inspiratory branch.

14. The wye-piece connector of claim 2, wherein the conduit end of the inspiratory branch is tapered on at least one of an inner surface or an outer surface such that the conduit end of the inspiratory branch is configured to be connected to an inspiratory conduit, and wherein the inspiratory conduit is in fluid communication with the inspiratory conduit port when the inspiratory conduit is connected to the conduit end of the inspiratory branch.

15. The wye-piece connector of claim 2, wherein the tip is generally cylindrical in shape.

16. The wye-piece connector of claim 4, wherein the free end of the patient end comprises a dual taper that allows the free end of the patient end to act as one or both of a female connector or a male connector.

17. The wye-piece connector of claim 4, wherein the free end of the patient end comprises a solid wall between an inner surface and an outer surface of the patient end.

18. The wye-piece connector of claim 4, wherein the free end of the patient end comprises a wall gap between an inner surface and outer surface of the patient end.

19. The wye-piece connector of claim 8, wherein the angle between the axis of the inspiratory branch and the axis of the expiratory branch is between 10 and 90 degrees.

20. The wye-piece connector of claim 8, wherein the angle between the axis of the inspiratory branch and the axis of the expiratory branch allows the wye-piece connector to direct flow from the inspiratory branch towards the patient end.

21. The wye-piece connector of claim 15, wherein the inspiratory branch further comprises an inner surface diameter that is different at the conduit end of the inspiratory branch than at the tip of the inspiratory branch.

22. The wye-piece connector of claim 21, wherein the inner surface diameter at the tip of the inspiratory branch is narrower than the inner surface diameter at the conduit end of the inspiratory branch.

23. The wye-piece connector of claim 22, wherein an inspiratory gas has a flow speed at the tip of the inspiratory branch that is greater than a flow speed at the conduit end of the inspiratory branch.

24. The wye-piece connector of claim 15, wherein the tip comprises a truncated cylindrical shape.

25. The wye-piece connector of claim 3, wherein the inner diameter of the second fluid passageway is smaller near the patient interface port than near the expiratory conduit port.

* * * * *